US011732014B2

(12) United States Patent
Baxter et al.

(10) Patent No.: US 11,732,014 B2
(45) Date of Patent: Aug. 22, 2023

(54) MODULATION OF SOLANACEAE FRUIT RIPENING

(75) Inventors: Charles Baxter, Bracknell (GB); Yu Pan, Loughborough (GB); Thomas Charles Hodgman, Loughborough (GB); Graham Barron Seymour, Loughborough (GB); Rebecca Cade, Durham, NC (US); Henricus Johannes Van Wijk, Saint-Saveur (FR); Glyn Bradley, Londonderry (IE); Laurent Grivet, Saint-Sauveur (FR); Laurie Boyden, Stanton, MN (US); Graham Ball, Nottingham (GB); Paul Fraser, Egham (GB)

(73) Assignee: Syngenta Participations AG, Basel (CH)

( * ) Notice: Subject to any disclaimer, the term of this patent is extended or adjusted under 35 U.S.C. 154(b) by 2989 days.

(21) Appl. No.: 13/825,203

(22) PCT Filed: Sep. 27, 2011
(Under 37 CFR 1.47)

(86) PCT No.: PCT/EP2011/066773
§ 371 (c)(1),
(2), (4) Date: Nov. 20, 2013

(87) PCT Pub. No.: WO2012/041856
PCT Pub. Date: Apr. 5, 2012

(65) Prior Publication Data
US 2014/0137296 A1 May 15, 2014

(30) Foreign Application Priority Data
Sep. 30, 2010 (EP) ..................... 10183748

(51) Int. Cl.
*A01H 6/82* (2018.01)
*C12N 15/82* (2006.01)
*C07K 14/415* (2006.01)

(52) U.S. Cl.
CPC .......... *C07K 14/415* (2013.01); *A01H 6/822* (2018.05); *C12N 15/825* (2013.01); *C12N 15/8249* (2013.01); *C12N 15/8261* (2013.01)

(58) Field of Classification Search
None
See application file for complete search history.

(56) References Cited

U.S. PATENT DOCUMENTS 7,960,612 B2 * 6/2011 Zhang .................. C07K 14/415
800/298
2005/0076410 A1 4/2005 Giovannoni
2009/0049566 A1 2/2009 Zhang

FOREIGN PATENT DOCUMENTS

EP WO2010020555 A1 2/2010
WO WO-2010020555 A1 * 2/2010 ........... C07K 14/415

OTHER PUBLICATIONS

Sequence Accession AWH37541, Jul. 9, 2009, sequence alignment is attached at the end of the office action. (Year: 2009).*
Matas, A.J. et al., Biology and genetic engineering of fruit maturation for enhanced quality and shelf-life. Current Opinion in Biotechnology. Apr. 1, 2009, p. 197-203, 20(2). London, GB.
Eriksson et al., "Effect of the Colorless non-ripening Mutation on Cell Wall Biochemistry and Gene Expression during Tomato Fruit Development and Ripening" Plant Physiology, Dec. 20014, vol. 136, pp. 4184-4197.
Manning et al., "A naturally occurring epigenetic mutation in a gene encoding an SBP-box transcription factor inhibits tomato fruit ripening," Nature Genetics, vol. 38, No. 8, Aug. 2006, pp. 948-952.
Thompson et al., "Molecular and Genetic Characterization of a Novel Pleiotropic Tomato-Ripening Mutant" Plant Physiology, Jun. 1999, vol. 120, pp. 383-389.
Vrebalov et al., "A MADS-Box Gene Necessary for Fruit Ripening at the Tomato Ripening-Inhibitor (Rin) Locus" Science 296, 343 (2002), 5 pages.
International Preliminary Report on Patentability in corresponding PCT Application No. PCT/EP2011/0066773 dated Apr. 2, 2013 (8 pages).
Notification of Transmittal of the International Search Report and the Written Opinion of the International Searching Authority, or the Declaration in corresponding PCT Application No. PCT/EP2011/066773 dated Feb. 21, 2012 (8 pages).

* cited by examiner

*Primary Examiner* — Weihua Fan
(74) *Attorney, Agent, or Firm* — Karen A. Magri

(57) ABSTRACT

The present invention relates to a transcription factor gene that plays a key role in Solanaceae fruit ripening. Plants overexpressing the gene have fruits with deeper pigmentation and ripen more rapidly than controls. The invention also relates to transgenic plants comprising said gene, and methods of making said plants.

2 Claims, 10 Drawing Sheets
Specification includes a Sequence Listing.

A

B

C

A

B

A

B

MODULATION OF SOLANACEAE FRUIT RIPENING

INTRODUCTION

The Solanaceae, also called nightshades, comprise over 3000 species many of which evolved in South America in dramatically varying habitats including rain forests and deserts.

The Solanaceae are economically the third most important plant taxon and the most valuable in terms of vegetable crops. They are the most variable in terms of agricultural utility, and include several fruit-bearing vegetables such as tomato and pepper.

Solanaceaous crops have been subjected to intensive human selection. This has allowed their use as models to study the evolutionary interface between plants and people. Some Solanaceae plants are important model systems for biology; these include tomato for fruit ripening and plant defense, tobacco for plant defense, and petunia for the biology of anthocyanin pigments. Tomato is an important model system for studying fruit ripening due to extensive genetic and genomic resources. Harvesting tomato fruit when ripening has set in would make maturity determination easier as it would be based on visible peel color and would assure full quality development. After harvest, ripening continues and softening advances, increasing the susceptibility of the fruit to handling damage and limiting the marketing period.

Ripening mutants in tomato such as Colourless non-ripening and ripening inhibitor have yielded important insights into an emerging genetic framework which regulates ripening and modulates fruit firmness (Thompson et al, 1999; Vrebalov et al, 2002; Eriksson et al, 2004; Manning et al, 2006). Delaying ripening and softening may be achieved by employing modified atmosphere packaging (MAP) which has been extensively studied as a simple and cheap method of prolonging shelf life of many fruits and vegetables including tomato (Batu & Thompson, 1998, Exama et al, 1993, Geeson et al, 1985), however it increases the cost of packaging and handling of fruits.

Existing methods to modulate fruit ripening in conventional plant breeding programs rely on screening fruit harvested from mature plants. Any identification of altered ripening in this scenario will largely be down to chance. Currently it is not financially viable or efficient to breed for altered ripening due to the cost and complexity of growing and phenotyping large numbers of plants.

Wild tomato species offer a rich and largely unexplored source of new genetic variation for breeders. Tanksley and Zamir (Frary et al, 2000; Fridman et al, 2004) have demonstrated that this source of genetic diversity can be used to understand the molecular basis of important fruit quality traits and provide new material for breeding.

Breeders are interested in learning about the developmental process of fruit ripening in order to breed new varieties of fruit and vegetables with altered pre and post harvest phenotypes. The manipulation of fruit ripening offers the potential to extend harvest windows and shelf life, thus reducing pre and post harvest losses in the production chain.

In tomatoes, the depth of pigmentation of tomato fruit is very important for consumer appeal and health and nutrition. There is therefore a need to discover genes which will allow the more efficient selection of early or delayed ripening phenotypes in tomato fruit. In addition, there is a need for selecting genotypes which produce fruit with high pigment content at the mature green stage. Such genes could serve as a molecular marker for fruit ripening phenotypes (speed to ripeness, pigment content) and offer the potential to manipulate speed to ripening and pigment content in tomato fruit.

Pepper fruit (*Capsicum annuum* L.) has been used since ancient times as a source of pigments to add to or change the colour of foodstuffs, making them more attractive and acceptable for the consumer. Pepper used as food colorant has traditionally been in the form of paprika (ground powder), although today oleoresins are widely used. Further information regarding pepper types, in particular sweet pepper types, can be found in Huh et al (2001).

SUMMARY OF THE INVENTION

The present invention relates to a transcription factor, and homologs thereof which are involved in the modulation of fruit ripening in the family Solanaceae. In tomato, the transcription factor in question (Le005930) was found by artificial neural network analysis on a tomato array dataset. Downstream analysis showed that this transcription factor had a ripening specific profile in tomato which increased dramatically between 40 dpa (days post anthesis) and 49 dpa. Le005930 has a high degree of homology to a two-component response regulator 2 (APRR2) from *Arabidopsis thaliana*. The gene encoding Le005930 (hereinafter also known as tomato APRR2 or tomato APRR2-like) is represented in SEQ ID NO:1. Tomato plants which overexpress the gene as shown in SEQ ID NO:1 have been shown herein to display enhanced fruit ripening properties whereas tomato plants which have downregulated levels of the gene display slower ripening properties.

To find the homologous gene in pepper (herein referred to as pepper APRR2 or pepper APRR2 like), the tomato EST sequence (SGN-U585565) was used to BLAST a pepper EST database. Further details of the isolation of the pepper APRR2 like sequence can be found in the examples section. Analysis has revealed the importance of the pepper APRR2 like gene in the pepper ripening process. Pepper APRR2 cDNA sequence can be found in SEQ ID NO: 2.

The present invention provides a vector comprising an isolated nucleotide sequence selected from the group consisting of: a) a nucleotide sequence set forth in SEQ ID NO:1 or SEQ ID NO: 2; b) a nucleotide sequence that is at least 80% identical to the nucleotide sequence of a); c) a nucleotide sequence comprising at least 21 consecutive nucleotides of the nucleotide sequence of a); d) a nucleotide sequence that hybridises under stringent conditions to the complement of any of nucleotide sequences a) to c); and e) a nucleotide sequence that is the complement to the nucleotide sequences of any one of a) to d). In one embodiment, the nucleotide sequence of step b) is at least 90% identical to the nucleotide sequence of a).

In one embodiment, the isolated nucleotide sequence is in the sense orientation. In another embodiment, the isolated nucleotide sequence is in the antisense orientation.

There is also provided a host cell which expresses a vector of the invention.

There is also provided a transgenic plant or part thereof comprising a host cell of the invention. In one embodiment, the transgenic plant or part thereof is a monocot. In another embodiment, the plant or part thereof is a dicot, for example a tomato, preferably *Solanum lycopersicum* or a pepper, preferably *Capsicum annuum*.

There is also provided a method for producing a transgenic plant comprising regenerating a plant from a host cell according to the invention.

There is also provided a cultivated plant or part thereof produced by a method according to the invention.

There is also provided a method of manipulating the speed of fruit ripening in fruit of a transgenic Solanaceae plant, preferably a tomato or a pepper plant comprising transforming said plant with a vector of the invention. In one embodiment, the speed of fruit ripening is increased when compared with fruit from an untransformed plant. In another embodiment, the speed of fruit ripening is decreased when compared with fruit from an untransformed plant. In one embodiment, the speed of fruit ripening is measured at 40 to 49 dpa. In one embodiment the speed of fruit ripening is measured at the mature green stage of the transformed plant. In one embodiment, speed of fruit ripening is measured at the immature colour stage in pepper. There is also provided a method of manipulating fruit pigment content in fruit of a transgenic Solanaceae plant comprising transforming said plant with a vector of the invention. In one embodiment, the fruit pigment content is increased in a transformed plant compared with fruit from an untransformed plant. In one embodiment, the fruit pigment content is decreased compared with fruit from an untransformed plant. In one embodiment, the fruit pigment content is measured at 40 to 49 dpa. In one embodiment the fruit pigment is measured at the mature green stage of the transformed plant. In one embodiment, fruit pigment content is measured at the immature colour stage in pepper.

There is also provided a tomato plant or part thereof obtained by any method of the invention. There is also provided a method of detecting for genetic markers indicative of speed of ripening or of pigment content of fruit of a plant of the Solanaceae family, comprising isolating DNA from said plant and from one or both parents of said plant; screening for genetic markers in a region of said DNA at or near sequence corresponding to SEQ ID NO:1 or SEQ ID NO: 2; and determining co-inheritance of said markers from one or both parents to said individual.

There is also provided a genetic marker detectable by a method of the invention.

There is also provided use of a genetic marker of the invention for the production of a cultivated Solanaceae plant, preferably a tomato or pepper plant capable of bearing fruit.

There is also provided a cultivated Solanaceae plant or part thereof produced by a method of the invention.

There is also provided use of a cultivated Solanaceae plant or part thereof according to the invention in the fresh cut market or for food processing.

There is also provided use of an isolated nucleotide sequence of the invention in the manipulation of speed of ripening or of pigment content of fruit of a plant, preferably a tomato or pepper plant, wherein said manipulation is effected by genetic modification of said plant. There is also provided use of a method according to the invention, wherein said genetic modification is introduced by a method selected from the list consisting of transposon insertion mutagenesis, T-DNA insertion mutagenesis, TILLING, site-directed mutagenesis, directed evolution, and homologous recombination.

DETAILED DESCRIPTION OF THE INVENTION

Figure 1:
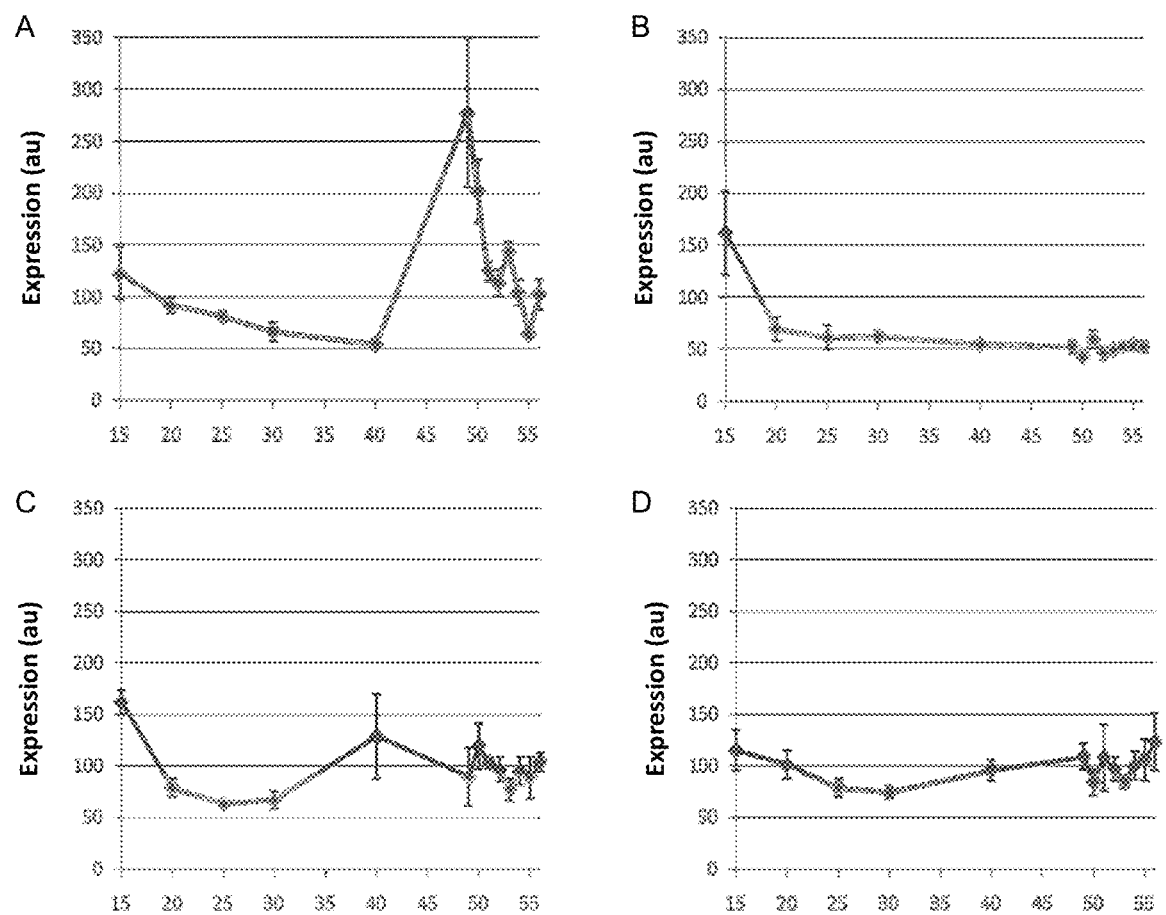
FIG. 1 Mean values for expression for Le 005930 in (A) WT, (B)RIN, (C) NOR and (D) CNR tomato mutants. Error bars are S.E.M., dpa=days post anthesis, au=arbitrary units.
Figure 2:
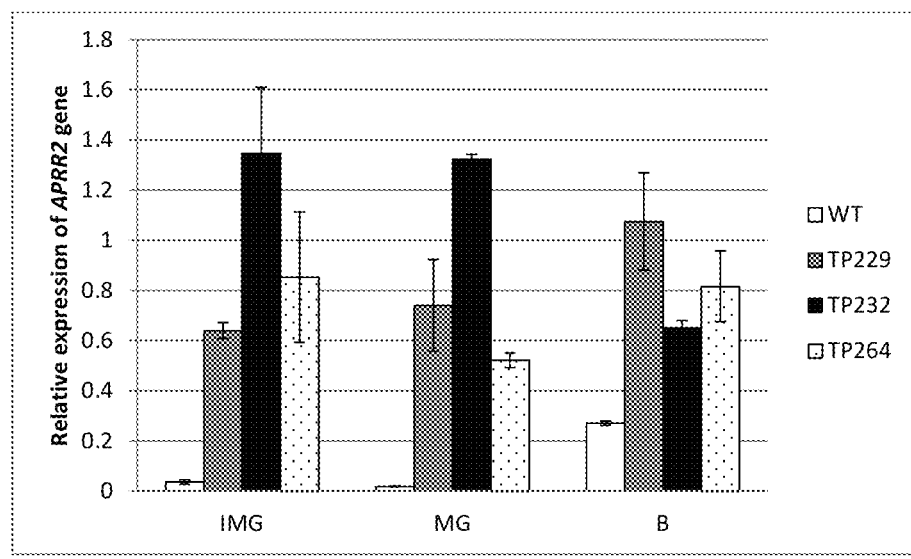
FIG. 2 qtPCR data showing relative expression of tomato lines overexpressing Le5390 (TP229, TP232 and TP264) at different stages of development compared with wild type (WT). IMG=immature green stage; MG=mature green stage; and B=breaker stage.

The present invention describes a transcription factor which can be expressed in a transgenic Solanaceae plant in order to modulate the ripening of a fruit growing on said plant. In tomato, this transcription factor was found as the result of artificial neural network analysis on a tomato array dataset. The homologue of tomato APRR2 was also found in pepper (see examples section). In particular, the invention relates to a vector comprising an isolated nucleotide sequence selected from the group consisting of a nucleotide sequence set forth in SEQ ID NO:1 (corresponding to tomato APRR2 cDNA sequence) or SEQ ID NO: 2 (corresponding to pepper APRR2 cDNA sequence). In another embodiment, the nucleotide sequence can be at least 80% identical, preferably at least 90% identical, more preferably at least 95%, more preferably at least 97%, most preferably at least 99% identical to the nucleotide sequence of a). In another embodiment, the nucleotide sequence may comprise at least 21 consecutive nucleotides of the nucleotide sequence of a). In another embodiment, the nucleotide sequence of the invention may hybridise under stringent conditions to the complement of any of nucleotide sequences a) to c). In another embodiment, the nucleotide sequence of the invention may be the complement to the nucleotide sequences of any one of a) to d).

Various DNA vectors constructs may be used to obtain a modulated fruit ripening phenotype according to the present invention. The DNA construct or an expression vector comprising same may further comprise regulatory elements, including, but not limited to, a promoter, an enhancer, and a termination signal. Among the most commonly used promoters are the nopaline synthase (NOS) promoter (Ebert et al., 1987), the octapine synthase (OCS) promoter, caulimovirus promoters such as the cauliflower mosaic virus (CaMV) 19S promoter (Lawton et al., 1987), the CaMV 35S promoter (Odell et al., 1985), and the figwort mosaic virus 35S promoter, the light inducible promoter from the small subunit of rubisco, the Adh, the sucrose synthase promoter, the R gene complex promoter and, the chlorophyll a/b binding protein gene promoter, etc. Other commonly used promoters are, the promoters for the potato tuber ADPGPP genes, the sucrose synthase promoter, Brittle gene promoter, the granule bound starch synthase promoter, the glutelin gene promoter, the maize waxy promoter, and Shrunken 2 promoter, the acid chitinase gene promoter, and the zein gene promoters. Many promoters are described in patent application WO 00/18963.

The term "3' non-coding sequences" refer to DNA sequences which are located downstream of a coding sequence and are understood to also include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

It will be appreciated by those skilled in the art that the components of the nucleic acid sequences and transformation vectors described herein are operatively linked, so as to result in expression of said nucleic acid or nucleic acid fragment. Techniques for operatively linking the components of the constructs and vectors of the present invention are well known to the skilled person and include the use of linkers, such as synthetic linkers, for example including one or more restriction enzyme sites. The vector could be an improved gateway binary high performance vector as described in Nakagawa et al (2007), for example vector pGWB405 which is suitable for use as an overexpression vector and is described in Example 3. In one embodiment, the gene for overexpression can be cloned in front of the CaMV 35S promoter. Other promoters as disclosed herein may also be suitable. For RNAi construct production, a fragment of coding sequence should preferably be cloned into a suitable vector. The vector can in some embodiments be a Gateway system RNAi vector. In one embodiment, the vector can be pK7GWIWG2.

There is also provided a vector as herein described, wherein the isolated nucleotide sequence is in the sense or antisense orientation, preferably in the sense orientation. There is also provided a host cell which expresses the vector as herein described.

There is also provided a transgenic plant or part thereof comprising the host cell as herein described. The skilled person would be well aquainted with methods for transforming a plant cell with nucleic acid sequences according to the present invention. The term "transformation" or "transforming" as used herein describes a process by which a foreign DNA, such as a DNA construct, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome. In some embodiments the nucleic acid sequence of the present invention is stably transformed into a plant cell. Various methods are known to the skilled person for introducing foreign genes into both monocotyledonous and dicotyledonous plants (eg Shimamoto K. et al., 1989). Efficient sweet pepper transformation mediated by the BABY BOOM transcription factor has recently been described by Heidmann et al., 2011.

The most well known methods of the stable integration of exogenous DNA into plant genomic DNA involves two main approaches.

The first such approach is direct DNA uptake. Various methods exist for direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues. The second approach is *Agrobacterium*-mediated gene transfer. The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation. A supplementary approach employs the *Agrobacterium* delivery system in combination with vacuum infiltration. The *Agrobacterium* system is especially useful in the generation of transgenic dicotyledenous plants.

The regeneration, development and cultivation of plants from single plant protoplast transformants or from various transformed explants is well known to the skilled person. The process typically includes the steps of selection of transformed cells, culturing those individualized cells through the usual stages of embryonic development through the rooted plantlet stage. Transgenic embryos and seeds are regenerated in a similar manner. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines, or pollen from plants of these important lines is used to pollinate regenerated plants. A transgenic plant of the present invention having a modulated fruit ripening phenotype can be cultivated using methods well known to the skilled person.

In one embodiment, the transgenic plant of the invention or part thereof can be a monocot. In another embodiment, the transgenic plant of the invention can be a dicot. In one embodiment, a dicot transgenic plant of the invention is a tomato plant, preferably *S. Lycopersicum* or a pepper plant, preferably *C. annuum*.

There is also provided a method for producing a transgenic plant comprising regenerating a plant from the host cell according to the invention. For instance, a nucleic acid sequence can be transferred by crossing a donor plant with a recipient plant i.e. by introgression, by transformation, by protoplast fusion, by a doubled haploid technique, by embryo rescue, or by any other nucleic acid transfer system, followed by selection of offspring plants comprising one or more of the presently disclosed QTLs and exhibiting increased fruit firmness. For transgenic methods of transfer, a nucleic acid sequence comprising a gene involved in modulating fruit firmness can be isolated from the donor plant using methods known in the art, and the thus isolated nucleic acid sequence can be transferred to the recipient plant by transgenic methods, for instance by means of a vector, in a gamete, or in any other suitable transfer element, such as a ballistic particle coated with the nucleic acid sequence.

Plant transformation generally involves the construction of an expression vector that will function in plant cells. In the presently disclosed subject matter, such a vector comprises a nucleic acid sequence that comprises an isolated nucleic acid sequence of the invention, which vector can comprise a gene conferring an increased fruit ripening phenotype that is under control of, or operatively linked to, a regulatory element such as a promoter. The expression vector can contain one or more such operably linked gene/regulatory element combinations, provided that at least one of the genes contained in the combinations enhances speed of ripening. The vector(s) can be in the form of a plasmid, and can be used, alone or in combination with other plasmids, to provide transgenic plants that have enhanced ripening speed using transformation methods known in the art, such as the *Agrobacterium* transformation system as described herein.

There is also provided a cultivated plant or part thereof produced by a method according to the invention.

There is also provided a method of manipulating the speed of fruit ripening in fruit of a transgenic Solanaceae plant comprising transforming said plant with a vector of the invention. In one embodiment the speed of fruit ripening is increased when compared with fruit from an untransformed plant. In one embodiment fruit of a transformed plant, preferably a tomato plant, reaches the mature green stage significantly earlier than the untransformed control plant. In one embodiment, fruit of a transformed plant, preferably a pepper plant, reaches the immature colour stage significantly earlier than fruit of an untransformed plant.

In one embodiment the speed of fruit ripening is decreased when compared with fruit from an untransformed plant.

In one embodiment the speed of fruit ripening is measured at 40 to 49 dpa. In one embodiment the speed of fruit ripening is measured at the mature green stage of the transformed plant. In one embodiment, the speed of pepper fruit ripening is measured at the immature colour stage of the transformed plant.

There is also provided a method of manipulating fruit pigment content in fruit of a transgenic Solanaceae plant comprising transforming said plant with the vector of the invention.

In one embodiment the fruit pigment content is increased compared with fruit from an untransformed plant.

In one embodiment the fruit pigment content is decreased compared with fruit from an untransformed plant.

In one embodiment the fruit pigment content is measured at 40 to 49 dpa. In one embodiment the fruit pigment content is measured at the mature green stage of the transformed plant. In one embodiment, the fruit pigment content is measured at the immature colour stage in pepper.

There is also provided a Solanaceae plant or part thereof obtained by any the method of the invention.

There is also provided a method of detecting for genetic markers indicative of speed of ripening or of pigment content of fruit of a plant of the Solanaceae family, comprising a) isolating DNA from said plant and from one or both parents of said plant; b) screening for genetic markers in a region of said DNA at or near sequence corresponding to SEQ ID NO:1 or SEQ ID NO: 2; and c) determining co-inheritance of said markers from one or both parents to said individual.

The skilled person will realise that a sample from virtually any plant tissue is suitable for genomic DNA assays. For example, convenient samples include tissues obtained from roots, leaves, stem, and fruit and parts thereof. Assays of cDNA or mRNA involve obtaining tissue sample from an organ in which the target nucleic acid is expressed. In some embodiments, the genomic DNA sample is obtained from leaves or roots and, in some cases, be further processed before the detecting step e.g. the DNA in the cell or tissue sample may be separated from other components of the sample, or may be amplified, etc.

In general, if the alteration is located in a gene, it may be in a noncoding or coding region of the gene. If located in a coding region the alteration may result in an amino acid alteration. Such a change may or may not have an effect on the function or activity of the encoded polypeptide. If the change is located in a non-coding region it can cause alternative splicing, which also may or may not have an effect on the encoded protein activity or function.

It should be understood that identifying markers associated with the modulated fruit ripening phenotype by detecting a variant gene product(s) are also encompassed within the scope of the present invention. A "variant gene product" as used herein refers to a gene product which is encoded by an altered gene encoding tomato APRR2, including, but not limited to, a full length gene product as shown in SEQ ID NO:1, or encoded by an altered gene encoding pepper APRR2, including, but not limited to, a full length gene product as shown in SEQ ID NO: 2; an essentially full-length gene product thereof, a biologically active fragment of the gene product and a non-biologically non-active gene product. Biologically active fragments should be understood as including any portion of the full-length polypeptide which initiates transcription comparable to the wild type. A variant gene product is also intended to mean gene products which have altered expression levels or expression patterns which are caused, for example, by the variant allele of a regulatory sequence(s). As used herein, the term "regulatory sequence" includes promoters, enhancers and other expression control elements (e.g., polyadenylation signals). Such regulatory sequences are described, for example, in Goeddel (1990). Regulatory sequences include those which direct constitutive expression of a nucleotide sequence in many types of host cell and those which direct expression of the nucleotide sequence only in certain host cells (e.g., tissue-specific regulatory sequences). In some embodiments, the alteration is identified in a non-coding region such as an intron, a polyadenylation site and/or a leader sequence. In some other embodiments the alteration is identified in a regulatory sequence. Detection of alterations in the examined DNA normally requires amplification of the DNA taken from the candidate plant. Methods for DNA amplification are well known to the skilled person. Most commonly used method for DNA amplification is PCR (polymerase chain reaction). Additional suitable amplification methods include the ligase chain reaction (LCR), transcription amplification and self-sustained sequence replication, and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 15 respectively.

According to certain embodiments, identifying the at least one alteration is performed by a technique selected from the group consisting of: terminator sequencing, restriction digestion, allele-specific polymerase reaction, single-stranded conformational polymorphism analysis, genetic bit analysis, temperature gradient gel electrophoresis ligase chain reaction and ligase/polymerase genetic bit analysis.

In certain embodiments, the alteration in the gene sequence encoded by tomato APRR2 cDNA sequence as set forth in SEQ ID NO 1, or pepper cDNA APRR2 sequence as set forth in SEQ ID NO: 2 is identified by employing nucleotides with a detectable characteristic selected from the group consisting of inherent mass, mass tag, electric charge, hapten molecule, electric spin, radioactive isotope type bioluminescent molecule, chemiluminescent molecule, tagged nucleic acid molecule, protein molecule, light scattering/phase shifting molecule and fluorescent molecule.

There is also provided a genetic marker detectable by the method of the invention.

There is also provided the use of a genetic marker of the invention for the selection of a cultivated Solanaceae plant, preferably a tomato or pepper plant capable of bearing fruit.

There is also provided a cultivated tomato or pepper plant or part thereof selected by a method of the invention.

There is also provided the use of a cultivated tomato or pepper plant or part thereof according to the invention in the fresh cut market or for food processing.

There is also provided the use of the isolated nucleotide sequence of the invention in the manipulation of speed of ripening or of pigment content of fruit of a plant, preferably a tomato or pepper plant, wherein said manipulation is effected by genetic modification of said plant. There is also provided the use according to the invention, wherein said genetic modification is introduced by a method selected from the list consisting of transposon insertion mutagenesis, T-DNA insertion mutagenesis, TILLING, site-directed mutagenesis, directed evolution, and homologous recombination.

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

As used herein, the term "about" when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

An "allele" is understood within the scope of the invention to refer to alternative or variant forms of various genetic units identical or linked to different forms of a gene or of any kind of identifiable genetic element, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, chemical or structural modification, transcription regulation or post-translational modification/regulation. In a diploid cell or organism, the two alleles of a given gene or genetic element typically occupy corresponding loci on a pair of homologous chromosomes.

An allele linked to a quantitative trait may comprise alternative or variant forms of various genetic units including those that are identical or linked to a single gene or multiple genes or their products or even a gene disrupting or controlled by a genetic factor contributing to the phenotype represented by said QTL.

As used herein, the term "breeding", and grammatical variants thereof, refer to any process that generates a progeny individual. Breedings can be sexual or asexual, or any combination thereof. Exemplary non-limiting types of breedings include crossings, selfings, doubled haploid derivative generation, and combinations thereof.

As used herein, the term "construct" refers to an artificially assembled or isolated nucleic acid molecule which includes the gene of interest. A construct may include the gene or genes of interest, a marker gene (which in some cases can also be the gene of interest) and suitable regulatory sequences. The inclusion of regulatory sequences in a construct is sometimes optional, for example, such sequences may not be required in situations where the regulatory sequences of a host cell are to be used. The term construct includes vectors but should not be seen as being limited thereto.

A "cultivated tomato plant" or "cultivated pepper plant" is understood within the scope of the invention to refer to a plant that is no longer in the natural state but has been developed by human care and for human use and/or consumption. "Cultivated plants" are further understood to exclude those wild-type species which comprise the trait being subject of this invention as a natural trait and/or part of their natural genetics.

As used herein, the term "gene" refers to a hereditary unit including a sequence of DNA that occupies a specific location on a chromosome and that contains the genetic instruction for a particular characteristic or trait in an organism.

"Genetic engineering", "transformation" and "genetic modification" are all used herein as synonyms for the transfer of isolated and cloned genes into the DNA, usually the chromosomal DNA or genome, of another organism.

As used herein, the phrases "genetic marker", "DNA marker" or "molecular marker" are interchangeable and refer to a feature of an individual's genome (e.g. a nucleotide or a polynucleotide sequence that is present in an individual's genome) that is linked to one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs) restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs) among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes. A genetic or molecular marker can be physically located in a position on a chromosome that is distal or proximal to the genetic loci with which it is linked (i.e. is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a very low rate of recombination between the genetic marker and the locus of interest, the presently disclosed subject matter can also employ genetic markers that are physically within the boundaries of a genetic locus (e.g. inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g. a quantitative trait as defined herein). Thus, in some embodiments a genotype comprises a summary of one or more alleles present within an individual at one or more genetic loci of a quantitative trait. In some embodiments, a genotype is expressed in terms of a haplotype (defined herein below).

"Heterozygous" is understood within the scope of the invention to refer to unlike alleles at one or more corresponding loci on homologous chromosomes.

"Homozygous" is understood within the scope of the invention to refer to like alleles at one or more corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C. particularly between 45° C. and 65° C., but especially at 59° C. (regarding the definition of SSPE, SSC and Denhardts solution see Sambrook et al. (2001)). High stringency hybridization conditions as for instance described in Sambrook et al. (2001), are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Increase in fruit firmness" and "increased fruit firmness" are understood within the scope of the invention to mean tomato or pepper fruit which has an increased maximum load value, statistically significant at $P<0.05$ or $P<0.01$ compared to fruit from a control untransformed plant. Maximum load is defined as the value that represents the greatest load (in Newtons (N)) required to cause failure of tissue integrity.

As used herein, the terms "introgression", "introgressed" and "introgressing" refer to the process whereby genes, a QTL or haplotype of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

The term "isolated" as used herein means a) separated from at least some of the components with which it is usually associated in nature; b) prepared or purified by a process that involves human intervention; and/or c) not found in nature. In particular, "isolated" is used herein to describe a polynucleotide of the invention which has been to some extent separated from other compounds including, but not limited to other nucleic acids, carbohydrates and proteins (such as the enzymes used in the synthesis of the polynucleotide), or the separation of covalently "closed" polynucleotides from linear polynucleotides. A polynucleotide is substantially isolated when at least about 50%, more preferably between 60 and 75% of a sample exhibits a single polynucleotide sequence and conformation (a linear conformation versus a covalently closed one). The degree of polynucleotide isolation or homogeneity may be indicated by a number of means well known to the skilled person, such as agarose electrophoresis or polyacrylamide gel electrophoresis of a sample, followed by visualisation of a single polynucleotide band on a stained gel. Higher resolution can further be provided by using HPLC or other means well known to the skilled person.

As used herein, the term "linkage", and grammatical variants thereof, refers to the tendency of alleles at different loci on the same chromosome to segregate together more often than would be expected by chance if their transmission were independent, in some embodiments as a consequence of their physical proximity. Linkage is measured by percent recombination between loci (centimorgan, cM).

"Locus" is understood within the scope of the invention to refer to a region on a chromosome, which comprises a gene or any other genetic element or factor contributing to a trait.

As used herein, the term "marker allele" refers to an alternative or variant form of a genetic unit as defined herein above, when used as a marker to locate genetic loci containing alleles on a chromosome that contribute to variability of phenotypic traits.

"Marker-based selection" is understood within the scope of the invention to refer to e.g. the use of genetic markers to detect one or more nucleic acids from the plant, where the nucleic acid is linked to a desired trait to identify plants that carry genes, QTLs or haplotypes for desirable (or undesirable) traits, so that those plants can be used (or avoided) in a selective breeding program.

"Marker assisted selection" refers to the process of selecting a desired trait or desired traits in a cultivated plant or cultivated plants by detecting one or more nucleic acids from the cultivated plant, where the nucleic acid is linked to the desired trait.

As used herein, "marker locus" refers to a region on a chromosome, which comprises a nucleotide or a polynucleotide sequence that is present in an individual's genome and that is linked to one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as a probe.

"Nucleic acid" or "oligonucleotide" or "polynucleotide" or grammatical equivalents thereof used herein means at least two nucleotides covalently linked together. Oligonucleotides are typically from about 7, 8, 9, 10, 12, 15, 18, 20, 25, 30, 40, 50 or up to about 100 nucleotides in length. Nucleic acids and polynucleotides are polymers of any length, including longer lengths, e.g. 200, 300, 500, 1000, 2000, 3000, 5000, 7000, 10000, etc. A nucleic acid of the present invention will generally contain phosphodiester bonds, although in some cases, nucleic acid analogs are included that may have alternate backbones comprising, e.g. phosphoramidate, phosphorothioate, phosphorodithioate, or O-methylphosphoroamidite linkages (see Eckstein, 1991), and peptide nucleic acid backbones and linkages. Mixtures of naturally occurring nucleic acids and analogs can be used. Particularly preferred analogs for oligonucleotides are peptide nucleic acids (PNA).

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

As used herein, the expression "phenotype" or "phenotypic trait" refers to the appearance or other detectable characteristic of an individual, resulting from the interaction of its genome, proteome and/or metabolome with the environment.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calii, and the like.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

"Polymorphism" is understood within the scope of the invention to refer to the presence in a population of two or more different forms of a gene, genetic marker, or inherited trait or a gene product obtainable, for example, through alternative splicing, DNA methylation, etc.

As used herein, the term "population" means a genetically heterogeneous collection of plants sharing a common genetic derivation.

The term "probe" or "hybridization probe" as used herein defines a nucleic acid segment (or nucleotide analog segment, e.g., polynucleotide as defined herein) which can be used to identify a specific polynucleotide sequence present in samples. The nucleic acid segment comprises a nucleotide sequence complementary of the specific polynucleotide sequence to be identified by hybridization. "Probes" or "hybridization probes" as used herein are nucleic acids capable of binding in a base-specific manner to a complementary nucleic acid strand. Such probes include peptide nucleic acids, as described in Nielsen et al. (1991). Hybridizations are usually performed under "stringent conditions", as defined herein.

As used herein, the term "progeny" refers to the descendant(s) of a particular cross. Typically, progeny result from breeding of two individuals, although some species (particularly some plants and hermaphroditic animals) can be selfed (i.e. the same plant acts as the donor of both male and female gametes). The descendant(s) can be, for example, of the F1, the F2, or any subsequent generation.

The term "recipient tomato plant" or "recipient pepper plant" is used herein to indicate a plant that is to receive DNA obtained from a donor plant that comprises a QTL for modulation of fruit ripening. Said "recipient plant" may or may not already comprise one or more QTLs for modulation of fruit ripening, in which case the term indicates a plant that is to receive an additional QTL.

The term "natural genetic background" is used herein to indicate the original genetic background of a QTL. Such a background may for instance be the genome of a wild accession of tomato.

In this application, a "recombination event" is understood to mean a meiotic crossing-over. "Sequence Homology" or "sequence Identity" is used herein interchangeably. The terms "identical" or "percent identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection, if two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman (1981) in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so called optional parameters are left at their preset ("default") values. The deviations appearing in the comparison between a given sequence and the above described sequences of the invention may be caused for instance by addition, deletion, substitution, insertion or recombination. Such a sequence comparison can preferably also be carried out with the program fasta20u66" (version 2.0u65, September 1998 by William R. Pearson and the University of Virginia; see also W. R. Pearson (1990), appended examples and http://workbench.sdsc.edu/). For this purpose, the "default" parameter settings are used. Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g. total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

A "single nucleotide polymorphism" (SNP) is a DNA sequence variation occurring when a single nucleotide A, C, G, T in the genome (or other shared sequences as mitochondrial DNA) differs between a set (paired) chromosomes of an individual or differs between members of a species. The term "standard greenhouse conditions" and "standard conditions" refer to the conditions of light, humidity, temperature, etc whereupon plants are grown or incubated, for instance for the purpose of phenotypic characterization of fruit ripening, as being standard. More in general, the terms refer to standard and reference growth conditions with a photoperiod of 16 h (photosynthetic photon flux (PPF) 50 to 1000 μmol nv2 s1), preferably a regime of 8 hours dark, an air temperature of about 20° C. during the day and 18° C. at night, a water vapour pressure deficit of about 4.4 g m3 corresponding to a relative humidity (RH) of about 60%-85%, at atmospheric oxygen concentration and at atmospheric air pressure (generally 1008 hPa). Water and nutrients may be given drop wise near the stem, or in the form of spray or mist.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part 1 chapter 2 "Overview of principles of hybridization and the strategy of nucleic acid probe assays" Elsevier, New York. Generally, highly stringent hybridization and wash conditions are selected to be about 5° C. lower than the thermal melting point (Tm) for the specific sequence at a defined ionic strength and pH. Typically, under "stringent conditions" a probe will hybridize to its target subsequence, but to no other sequences.

The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on a filter in a Southern or Northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2 times SSC wash at 65° C. for 15 minutes (see Sambrook, infra, for a description of SSC buffer). Often, a high stringency wash is preceded by a low stringency wash to remove background probe signal. An example medium stringency wash for a duplex of for example more than 100 nucleotides, is 1 times SSC at 45° C. for 15 minutes. An example low stringency wash for a duplex of, e.g. more than 100 nucleotides, is 4-6 times SSC at 40° C. for 15 minutes. For short probes (e.g. about 10 to 50 nucleotides), stringent conditions typically involve salt concentrations of less than about 1.0M Na ion concentration, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs for example when a copy of a nucleic acid is created using the maximum codon degeneracy permitted by the genetic code.

As used herein, the term "tomato" preferably means *Solanum lycopersicum* but can also mean any plant, line or population formerly known under the genus name of Lycopersicon including but not limited to *L. cerasiforrne, L. cheesmanii, L. chilense, L. chmielewskii, L. esculentum* (now *S. pennellii*), *L. hirsutum, L. parviborum, L. pennellii, L. peruvianum, L. pimpinellifolium,* or *S. lycopersicoides*. The newly proposed scientific name for *L. esculentum* is *S. pennellii*. Similarly, the names of the wild species may be altered. *L. pennellii* has become *S. pennellii, L. hirsutum* may become *S. habrochaites, L. peruvianum* may be split into *S. 'N peruvianum'* and *S. 'Callejon de Huayles', S. peruvianum,* and *S. corneliomuelleri, L. parviflorum* may become *S. neorickii, L. chmielewskii* may become *S. chmielewskii, L. chilense* may become *S. chilense, L. cheesmaniae* may become *S. cheesmaniae* or *S. galapagense,* and *L. pimpinellifolium* may become *S. pimpinellifolium* (Knapp (2005)).

"Trait" is understood within the scope of the invention to refer to a characteristic or phenotype, for example modulation of fruit ripening. A trait may be inherited in a dominant or recessive manner, or may be monogenic or polygenic.

"Dominant" is understood within the scope of the invention to refer to an allele which determines the phenotype when present in the heterozygous or homozygous state.

A "recessive" allele is only displayed when present in the homozygous state.

"Isogenic" is understood within the scope of the invention to refer to cultivated plants which are genetically identical, except that they may differ by the presence or absence of a heterologous DNA sequence.

"Harvesting stage" is understood within the scope of the invention to mean the date of harvesting ie the date the fruit is removed from the plant.

"Immature colour stage" with respect to pepper is defined as the initial colour developed when the fruit has reached full size. In pepper, immature colour is defined as the colour before the breaker stage.

"Mature colour" in pepper is the colour the fruit finally develops. Pepper also passes through intermediate colours that are the same as the breaker stage in tomato (see below).

"Breaker stage" in pepper is when the colour starts changing from the immature colour.

"Ripe stage" in pepper is where the pepper reaches its final colour.

"Immature Green stage" with respect to tomatoes is defined as when the fruits are unripe and still growing in size. This stage is understood to be the first stage in the ripening process.

"Mature green stage" with respect to tomatoes is defined as when the fruit is fully expanded mature, but unripe and follows the "immature green stage" in the ripening process. Mature green tomatoes have a white to yellow "star" on the blossom end. Traditional tomatoes harvested at the mature green stage are best suited for the commercial fresh market because they tolerate rough handling better than the riper stages and hold their shape the longest in storage, shipping, and on the supermarket shelf; however they somehow lack full aroma and taste.

"Breaker stage" with respect to tomatoes is defined as first sign of red colour in the fruit, typically it occurs within 24 hours of the mature green stage. Tomatoes that are harvested at the "Breaker stage" usually have better flavor and taste but they have reduced firmness and are slightly less suitable for handling, packaging and transportation than tomatoes at the mature green stage.

"Red ripe stage" with respect to tomatoes is defined as when the fruits are fully red, with no sign of green colour. These fruits have reached their optimum in taste and flavor but they cannot be transported because of their lack of firmness and they do not tolerate much handling.

"Genetic element" and "genetic element, or part thereof" are understood within the scope of the invention to mean a gene or part thereof that is capable of contributing to the firmness of the fruits of the plant by influencing expression of the firmness trait at the level of the DNA itself, at the level of translation, transcription and/or activation of a final polypeptide product, i.e., to regulate metabolism in tomato fruit flesh leading to the phenotypic expression of the genotype.

"Inner pericarp" and "outer pericarp" are understood within the scope of the invention to mean fruit tissue where the outer pericarp is the layer (approximately 2 mm) immediately below the outer epidermis and above the vascular tissue layer. The inner pericarp is from 3 mm up to 10 mm below the vascular layer and before the inner epidermis.

"Harvesting slot" is understood within the scope of the invention to mean the period of time from the harvesting stage until when the fruit is too ripe to be harvested for the purposes of commercial sale. Typically, the harvesting slot starts at mature green stage and continues until the breaker stage plus two to five days, depending on the cultivar and environmental conditions.

"linked to" and "characterized by" or "associated with" at least one of the DNA markers of the present invention is understood within the scope of the invention to mean a DNA sequence that is genetically linked, to the gene of interest responsible for the modulation of fruit ripening trait and wherein a specific marker sequence is linked to a particular allele of that gene. When two markers/sequences are said to be genetically linked, the recombination frequency between the two markers/sequences are low and it can be expected that both these markers/sequences are inherited jointly. For the population of plants described herein, markers named as linked to the QTLs are a distance of 1 cM or less away. Markers that are 1 cM distance apart from each other have a 1% chance of being separated from each other due to a recombination event in a single generation.

"Increase" or "decrease" in fruit ripening are understood within the scope of the invention to mean fruit which has an increased/decreased Colour Index (for example as described in the Examples section), or increased/decreased fruit texture statistically significant at $P<0.05$ or $P<0.01$ compared to fruit from a control untransformed plant.

Maximum load is defined as the value that represents the greatest load (in Newtons (N)) required to cause failure of tissue integrity.

"control tomato plant" or "control pepper plant" is understood within the scope of the invention to mean a plant that has the same genetic background as the cultivated plant of the present invention wherein the control plant does not overexpress the genetic elements—or part thereof—of the present invention linked to modulation of fruit ripening. In particular a control plant is a plant belonging to the same plant variety as the transformed plant. The control plant is grown for the same length of time and under the same conditions as the cultivated plant of the present invention. Plant variety is herein understood according to definition of UPOV. Thus a control plant may be an inbred line or a hybrid provided that they have the same genetic background as the plant of the present invention except the control plant does not overexpress the genetic element—or part thereof—of the present invention linked to modulation of fruit ripening.

"anthesis" is understood within the scope of the invention to mean the period during which the flower is fully open and pollen is released.

"Processed food" is understood within the scope of the invention to mean food which has been altered from its natural state. Methods used for processing food include but are not limited to canning, freezing, refrigeration, dehydration and aseptic processing.

"Fresh cut market" is understood within the scope of the invention to mean vegetables on the market which have been minimally processed.

EMBODIMENTS

Embodiment number is listed on the left hand side of each line in this section.

1. A vector comprising an isolated nucleotide sequence selected from the group consisting of:
    a) A nucleotide sequence set forth in SEQ ID NO:1 or SEQ ID NO: 2 or part thereof;
    b) A nucleotide sequence that is at least 80% identical to the nucleotide sequence of a);
    c) A nucleotide sequence comprising at least 21 consecutive nucleotides of the nucleotide sequence of a);
    d) A nucleotide sequence that hybridises under stringent conditions to the complement of any of nucleotide sequences a) to c); and
    e) A nucleotide sequence that is the complement to the nucleotide sequences of any one of a) to d).
2. A vector comprising an isolated nucleotide sequence as set forth in SEQ ID NO:1 or SEQ ID NO: 2 or part thereof.

3. A vector comprising an isolated nucleotide sequence that is at least 80% identical to SEQ ID NO:1 or SEQ ID NO: 2.
4. A vector comprising an isolated nucleotide sequence that is at least 90% identical to SEQ ID NO:1 or SEQ ID NO: 2.
5. A vector comprising an isolated nucleotide sequence that is at least 95% identical to SEQ ID NO:1 or SEQ ID NO: 2.
6. A vector comprising an isolated nucleotide sequence comprising at least 21 consecutive nucleotides of SEQ ID NO:1 or SEQ ID NO: 2.
7. A vector comprising an isolated nucleotide sequence that hybridises under stringent conditions to the complement of SEQ ID NO:1 or SEQ ID NO: 2.
8. A vector comprising an isolated nucleotide sequence that hybridises under stringent conditions to the complement of a nucleotide sequence that is at least 80% identical to SEQ ID NO:1 or SEQ ID NO: 2.
9. A vector comprising an isolated nucleotide sequence that hybridises under stringent conditions to the complement of a nucleotide sequence that is at least 90% identical to SEQ ID NO:1 or SEQ ID NO: 2.
10. A vector comprising an isolated nucleotide sequence that hybridises under stringent conditions to the complement of a nucleotide sequence comprising at least 21 consecutive nucleotides of SEQ ID NO:1 or SEQ ID NO: 2.
11. A vector comprising an isolated nucleotide sequence that is the complement to the isolated nucleotide sequence comprised in the vector of embodiment 2.
12. A vector comprising an isolated nucleotide sequence that is the complement to the isolated nucleotide sequence comprised in the vector of embodiment 3.
13. A vector comprising an isolated nucleotide sequence that is the complement to the isolated nucleotide sequence comprised in the vector of embodiment 4.
14. A vector comprising an isolated nucleotide sequence that is the complement to the isolated nucleotide sequence comprised in the vector of embodiment 5.
15. A vector comprising an isolated nucleotide sequence that is the complement to the isolated nucleotide sequence comprised in the vector of embodiment 6.
16. A vector comprising an isolated nucleotide sequence that is the complement to the isolated nucleotide sequence comprised in the vector of embodiment 7.
17. A vector comprising an isolated nucleotide sequence that is the complement to the isolated nucleotide sequence comprised in the vector of embodiment 8.
18. A vector comprising an isolated nucleotide sequence that is the complement to the isolated nucleotide sequence comprised in the vector of embodiment 9.
19. A vector comprising an isolated nucleotide sequence that is the complement to the isolated nucleotide sequence comprised in the vector of embodiment 10.
20. The vector of embodiments 1 to 19, wherein the isolated nucleotide sequence is in the sense orientation.
21. The vector of embodiments 1 to 19, wherein the isolated nucleotide sequence is in the antisense orientation.
22. A host cell which expresses the vector of embodiments 20 or 21.
23. A transgenic plant or part thereof comprising the host cell of embodiment 22.
24. The transgenic plant or part thereof of embodiment 23, wherein the plant is a monocot.
25. The transgenic plant or part thereof of embodiment 23, wherein the plant is a dicot.
26. The transgenic plant or part thereof of embodiment 25, wherein the plant is a member of the family Solanaceae.
27. The transgenic plant or part thereof of embodiment 26, wherein the plant is a tomato, preferably *Solanum lycopersicum*.
28. The transgenic plant or part thereof of embodiment 26, wherein the plant is a pepper, preferably *Capsicum annuum*.
29. The transgenic plant or part thereof of embodiment 27 or 28, wherein the fruit of the plant has a significantly increased TCI at the mature green stage, compared with fruit from a wild type plant of the same genetic background which does not contain a vector expressing the vector of embodiment 20.
30. The transgenic plant or part thereof of embodiment 27 or 28, wherein the fruit, preferably pepper fruit, of the plant has a significantly increased TCI at the immature colour stage, compared with fruit from a wild type plant of the same genetic background which does not contain a vector expressing the vector of embodiment 20.
31. The transgenic plant or part thereof of embodiment 27 or 28, wherein the plant has significantly increased chlorophyll in the outer pericarp at the mature green stage, compared with a wild type plant of the same genetic background which does not contain a vector expressing the vector of embodiment 20.
32. The transgenic plant or part thereof of embodiment 27 or 28, wherein the fruit, preferably pepper fruit, of the plant has significantly increased chlorophyll in the outer pericarp at the immature colour stage, compared with a wild type plant of the same genetic background which does not contain a vector expressing the vector of embodiment 20.
33. The transgenic plant or part thereof of embodiment 27 or 28, wherein the plant has plastids of significantly increased size in the outer pericarp at the mature green stage, compared with a wild type plant of the same genetic background which does not contain a vector expressing the vector of embodiment 20.
34. The transgenic plant or part thereof of embodiment 27 or 28, wherein the plant has plastids of significantly increased size in the outer pericarp at the immature colour stage, compared with a wild type plant of the same genetic background which does not contain a vector expressing the vector of embodiment 20.
35. The transgenic plant or part thereof of any one of embodiments 29 to 31, wherein the length of time taken to reach the mature green stage is significantly less than that compared with a wild type plant of the same genetic background which does not contain a vector expressing the vector of embodiment 20.

36. The transgenic plant or part thereof of any one of embodiments 29 to 31, wherein the length of time taken to reach the immature colour stage is significantly less than that compared with a wild type plant of the same genetic background which does not contain a vector expressing the vector of embodiment 20.
37. A method for producing a transgenic plant comprising regenerating a plant from the host cell according to embodiment 22.
38. The method for producing a transgenic plant according to embodiment 37, wherein the transgenic plant is a monocot.
39. The method for producing a transgenic plant according to embodiment 37, wherein the plant is a dicot.
40. The method according to embodiment 39, wherein the plant is a member of the family Solanaceae.
41. The method according to embodiment 40, wherein the plant is a tomato, preferably *Solanum lycopersicum*.
42. The method according to embodiment 40, wherein the plant is a pepper, preferably *Capsicum annuum*
43. A cultivated Solanaceae plant or part thereof, preferably seed, produced by the method according to embodiment 37 to 42.
44. The cultivated plant or part thereof of embodiment 43, wherein the plant is tomato, preferably *Solanum lycopersicum*.
45. The cultivated plant or part thereof of embodiment 43, wherein the plant is pepper, preferably *Capsicum annuum*.
46. A method of manipulating the speed of ripening in fruit of a transgenic Solanaceae plant comprising transforming said plant with the vector of embodiments 1 to 21.
47. A method of manipulating the speed of ripening in fruit of a transgenic Solanaceae plant comprising transforming said plant with the vector of embodiments 1 to 20, wherein the speed of fruit ripening is increased when compared with tomato fruit from an untransformed tomato plant.
48. A method of manipulating the speed of ripening in fruit of a transgenic Solanaceae plant comprising transforming said plant with the vector of embodiments 1 to 21, wherein the speed of fruit ripening is measured at the mature green stage.
49. A method of manipulating the speed of ripening in fruit of a transgenic Solanaceae plant, preferably a pepper plant, comprising transforming said plant with the vector of embodiments 1 to 21, wherein the speed of fruit ripening is measured at the immature colour stage
50. A method of manipulating fruit pigment content in fruit of a transgenic Solanaceae plant comprising transforming said plant with the vector of embodiments 1 to 21.
51. A method of manipulating fruit pigment content in fruit of a transgenic Solanaceae plant comprising transforming said plant with the vector of embodiments 1 to 20, wherein the fruit pigment content is significantly increased compared with fruit from an untransformed plant at the mature green stage.
52. A method of manipulating fruit pigment content in fruit of a transgenic Solanaceae plant, preferably a pepper plant, comprising transforming said plant with the vector of embodiments 1 to 20, wherein the fruit pigment content is significantly increased compared with fruit from an untransformed plant at the immature colour stage.
53. A method of manipulating fruit pigment content in fruit of a transgenic Solanaceae plant comprising transforming said plant with the vector of embodiments 1 to 21, wherein the fruit pigment content is significantly decreased compared with fruit from an untransformed plant.
54. A method of manipulating fruit pigment content in fruit of a transgenic Solanaceae plant comprising transforming said plant with the vector of embodiments 1 to 21, wherein the fruit pigment content is measured at the mature green stage.
55. A method of manipulating fruit pigment content in fruit of a transgenic Solanaceae plant, preferably a pepper plant, comprising transforming said plant with the vector of embodiments 1 to 21, wherein the fruit pigment content is measured at the immature colour stage
56. The method according to embodiments 46 to 55 wherein the plant is tomato, preferably *Solanum lycopersicum*.
57. The method according to embodiments 46 to 55 wherein the plant is pepper, preferably *Capsicum annuum*.
58. Solanaceae plant or part thereof obtained by the method of any one of embodiments 49 to 57.
59. A method of detecting for genetic markers indicative of speed of ripening or of pigment content of fruit of a plant of the Solanaceae family, comprising:
   a. isolating DNA from said plant and from one or both parents of said plant;
   b. screening for genetic markers in a region of said DNA at or near sequence, preferably within one centimorgan, corresponding to SEQ ID NO:1 or SEQ ID NO: 2; and
   c. determining co-inheritance of said markers from one or both parents to said individual.
60. A method according to embodiment 59, wherein the plant of the Solanaceae family is tomato, preferably *Solanum lycopersicum*, capable of bearing fruit.
61. A method according to embodiment 59, wherein the plant of the Solanaceae family is pepper, preferably *Capsicum annuum*, capable of bearing fruit.
62. A genetic marker detectable by the method of embodiments 59 to 61.
63. A genetic marker according to embodiment 62, wherein the mutation is a G to A substitution at position 1350 of SEQ ID NO: 15 or position 4379 of SEQ ID NO: 16.
64. Use of the genetic marker of embodiment 63, for the selection of a cultivated Solanaceae plant, preferably a pepper plant, capable of bearing fruit.
65. Use of a cultivated Solanaceae plant or part thereof according to embodiment 58 in the fresh cut market or for food processing.

66. Use of the isolated nucleotide sequence comprised in the vector of embodiments 1 to 21, in the manipulation of speed of ripening or of pigment content of fruit of a plant, preferably a Solanaceae plant, wherein said manipulation is effected by genetic modification of said plant.

67. Use according to embodiments 64 or 66, wherein the plant is tomato, preferably *Solanum lycopersicum*.

68. Use according to embodiments 64 or 66, wherein the plant is pepper, preferably *Capsicum annuum*.

69. Use according to embodiment 66, wherein said genetic modification is introduced by a method selected from the list consisting of transposon insertion mutagenesis, T-DNA insertion mutagenesis, TILLING, site-directed mutagenesis, directed evolution, and homologous recombination.

EXAMPLES

The following examples are presented in order to more fully illustrate some embodiments of the invention. They should in no way be construed, however, as limiting the broad scope of the invention. One skilled in the art can readily devise many variations and modifications of the principles disclosed herein without departing from the scope of the invention.

Example 1

Tomato Gene Identification and Network Inference

The Le005930_at gene (herein also referred to as tomato APRR2, or tomato APRR2 like) was identified as the result of a neural network analysis on a tomato array dataset. RNA samples were prepared from Ailsa Craig Wild type and nor, rin and Cnr mutant alleles in an Ailsa Craig background at different tomato fruit development stages. Ripening was performed according to standard methods. Expression values of Le005930_at were obtained using Syngenta's custom 23 k Affymetrix tomato genechip. The microarray data was normalised in the R statistical environment by the RMA method (Irizarry et al 2003) available in the affy Bioconductor package (Gautier et al 2004) being run via the affylmGUI package (Smyth 2005).

Transcription factors were selected for downstream analysis. Le005930_at was found to have a ripening specific expression profile dramatically increasing between 40 dpa and 49 dpa (FIG. 1a) which corresponds to the first appearance or red colouration. This increase was not present in any of the 3 mutant lines (FIG. 1a-c), where expression never approached the levels seen in wild type. Artificial neural network (ANN) analysis was carried out on 2 time points of data (40 dpa and 54 dpa). Le005930_at was detected as a hub.

Gene Expression Changes in Le005930 over expressors were measured. Analysis of the entire developmental series at growth stages mature green (MG) and breaker (B) against wild type fruits at the same stages revealed that a large number of genes are up- and down-regulated in the transgenic lines. Of the up-regulated genes many are fruit-ripening related, but expressed earlier in the overexpression lines. For example, in the MG stage LeEXP1 is almost 20 fold more highly expressed and polygalacturonase 10 fold higher than in MG WT. Expression of the NOR transcription factor is 19 fold higher than MG WT. Genes encoding cell wall enzymes that are normally expressed at their highest level in mature green fruit, e.g. some members of the xyloglucan endotransglucosylase/hydrolase family (Solyc02g091920, XTH7) show reduced expression in MG transgenics in comparison to wild type. These data indicate that up-regulating APRR2 like gene from chromosome 8 in tomato massively induces ripening-related gene expression.

TABLE 1

| Sol ID | Annotation | Differential fold expression in the overexpresser (log FC) | Remarks regarding normal ripening |
|---|---|---|---|
| Solyc04g071650 | Cellulose synthase | −1.78468 | Highest at mature green |
| Solyc07g052980 | XTH16 | −1.94747 | Highest at mature green |
| Solyc03g093080 | XTH3 and 4 copies in same region | −2.06438 | Highest breaker and red ripe |
| Solyc02g088100 | LeEXP5 | −2.17115 | Highest at mature green |
| Solyc10g005960 | FLA | −2.1184 | Highest at mature green |
| Solyc02g091920 | XTH7 | −3.28676 | Highest in mature green |

Overall, the array data shows that many genes that are normally positively associated with ripening are up-regulated in the tomato APRR2 gene over expresser very early (ie at the mature green stage) or in some cases genes that are down-regulated at the mature green stage appear to be suppressed at the mature green stage to a greater extent in the over expresser. For example, NOR that is normally lowly expressed at mature green is forced in the over expresser. This is very strong evidence that the tomato APRR2 gene forces early ripening when overexpressed.

Example 2

Tomato APRR2 Like Gene Sequence Information

The probe sequence from Le005930 was identical to SGN Unigene SGN-U585565. The gene represented by Le005930 was identified as most closely related to a two-component response regulator-like APRR2 from *Arabidopsis thaliana*.

Example 3

Generation of Transgenic Tomato Plants

Construct and Vector Details

Constructs were generated to over express and down regulate this APRR2-related gene. The sequence of the over expression and RNAi constructs are provided in SEQ ID NO:1 and SEQ ID NO:3 respectively.

SEQ ID NO: 1
GACCCACCTAACTATAATCAACAAACGACCCTTAAAAGAAGAAGAAAAAACAAGAACAGATGA

GCTAAGTCTTCTTCATTTCCCAAGAGATACAGGATTGAATAGTTAATGACTGATTAAAAAGTGAC

CGAGTTGGAGGGACTAAAAAGGATGCCTTTTTAGAAATGATTTGCATTGAGAATGAATTATTGG

GTTGGAAAGATTTCCCAAAGGGGCTTAAAGTCCTACTTCTTGATGAAGATAGCAACTCTGCTGC

TGAGATGAAATCAAGGCTTGAGAAAATGGACTACATAGTCTACTCGTTCTGCAACGAGAGCGA

AGCTTTGACTGCAATCTCAAGCAAATCCGAGGGCTTTCATGTTGCCATTGTGGAGGTAAGTGCA

GGCAACAGTGATGGGGTTCTACGGTTTCTTGAAAGTGCCAAAGATCTACCAACTATAATGACAT

CAAATATACATTCTCTTAGTACCATGATGAAATGTATTGCGCTAGGCGCAGTTGAGTTCCTTCAG

AAACCATTGTCAGATGATAAACTCAAAAATATATGGCAGCATGTAGTTCACAAGGCATTCAATA

CTAGAAAGGATGTGTCCAAATCACTTGAGCCGGTAAAAGATTCTGTCCTCTCGATGCTGCAGTT

ACAACTAGAAATGGGTGAAGCAGATGACAAAAGTTCAAATGGAACAGAACCTCCCACTGCAGT

AGCGGAAAGCAATACTGAACAGTCATCGGGCTGTGATAAATACCCTGCTCCCTCAACCCCACAA

TTGAAACAAGGAGTGCGATCCGTCGATGATGGTGACTGCCATGATCATACTATCTTCTCAACTG

ACCAAGACAGTGGGGAACATGATGCTGACACTAAATCCGTCGAAACTACTTATAACAATTCACT

TGCTGAGAATAATGTCCAAACAAGTCCTACTGTACAGCAAGGAGATATTATTTTGAAAGAGGAT

AATGTTTCATCTCCTGATCTAAAGACGGAGACTGATATCGCTACCACTTCACGAAGTAACGACTG

CCCTGACAATAGCATTATGCATTCTGCTGAACCTAGTAAAGCATCTGGTCCTCATAGTTCAAATG

GGACTAAATCCAATAGGAAGAAGATAAAGGTAGATTGGACACCTGAACTACACAAGAAGTTTG

TTCAAGCAGTAGAGCAACTCGGTATAGATCAAGCCATTCCTTCTCGAATACTGGACCTGATGAA

AGTAGAGGGCTTAACGAGACATAACGTAGCTAGCCATCTCCAGAAATACAGAATGCATCGAAA

GCAAATTTTGCCAAAGGAAGTAGAAAGAAGATGGCCTAATCCGCAACCAATAGATTCAGTCCA

AAGAAGTTACTATCCTCATAAACCTATCATGACATTCCCACAATATCATTCTAATCATGTTGCCCC

AGGTGGTCAGTTCTATCCTGCTTGGGTAACACCAGCAAGTTATCCGAACGGTTTACAAGTGTGG

GGTTCACCTTACTATCCGGGATGGAAACCTGCAGAGACTTGGCACTGGACGCCTCGTCCAGAGC

TGCATGCTGATACATGGGGCTCCCCTATCATGTCACCGTCGCTTGGATCATATCCACCATATCCT

CAGAATGCTGGAGTGTACCGGCCACATGGAACACATAACAGATATAGCATGCTAGAGAAGTCG

TTTGATCTTCACCCGGCGGATGAGGTGATTGATAAAGTAGTAAAAGAGGCAATAACCAAACCAT

GGTTACCACTTCCTTTGGGCCTAAAAGCTCCTTCAACGGAGAGCGTTCTTGACGAACTTTCTAGA

CAAGGGATCTCAACCATTCCTTCACAAATCAACGACTCCCGTTGTCGGAGATGAGATGACATGT

CATTCTAATTTTTTTTGGGTCCCATAGTTGGTGCATGTCAAAAAAAAATAATAATCTCCAATTACT

TGATGGACATATGTACCATGACATTACCCAGTGACCCGAGTGACCCACGCGTATGGCATTGACT

CGACGGTCAAAATCGAGTTGTTGTAAATAATGGACCCAAATATGGGTTTTCCCTTTTTTGTTGGC

CCAATTTTAGATGTTTGGGCCGATGAGTGTGCTCCATT

SEQ ID NO: 3
CACAATATCATTCTAATCATGTTGCCCCAGGTGGTCAGTTCTATCCTGCTTGGGTAACACCAGCA

AGTTATCCGAACGGTTTACAAGTGTGGGGTTCACCTTACTATCCGGGATGGAAACCTGCAGAGA

CTTGGCACTGGACGCCTCGTCCAGAGCTGCATGCTGATACATGGGGCTCCCCTATCATGTCACC

GTCGCTTGGATCATATCCACCATATCCTCAGAATGCTGGAGTGTACCGGCCACATGGAACACAT

AACAGATATAGCATGCTAGAGAAGTCGTTTGATCTTCACCCGGCGGATGAGGTGATTGATAAA

GTAGTA

The over-expression vector used was pGWB405 (Nakagawa T, Suzuki T, Murata S at el. Improved Gateway Binary Vectors: High-performance Vectors for CREATION of Fusion Constructs in Transgenic Analysis of Plants. Bioscience biotechnology Biochemistry, 71(8)2095-2010, 2007). For overexpression construct production, 2090 bp of the Le005930 sequence corresponding to the complete open reading frame were cloned in front of the CaMV 35S promoter using the Gateway clone system which avoids the need for restriction sites. Sequence attB1 (GGGGACAAGTTTGTACAAAAAAGCAGGCT) (SEQ ID NO:4) and attB2 (GGGGACCACTTTGTACAAGAAAGCTGGGT) (SEQ ID NO:5) was added at the 5' end of forward and reverse primers separately. The construct also contained the CaMV terminator at the opposite end. For RNAi construct production, a 326 bp fragment of the 3' coding sequence unique to the Le005930 gene was cloned into the Gateway system RNAi vector pK7GWIWG2 (I). The 326 bp fragment of 3' coding sequence used in this example starts from CACAATATCATTCTAATCAT (nucleotides 1 to 20 of SEQ ID NO: 3) and ends with AGGTGATTGATAAAGTAGTA (nucleotides 307 to 326 of SEQ ID NO: 3).

Genetic Transformation of Tomato (Micro-Tom)

Micro-Tom tomato seeds were obtained from Dr Andrew Thompson, Warwick HRI, UK. These tomato seeds are also publically available from the Tomato Genetics Resource Centre, Davis, Calif. Seeds were sterilized for 30 s in 70% ethanol, rinsed 3 times in sterile water followed by 10 minutes in 50% bleach and rinsed with sterile water 5-7 times. The seeds (50-100 seeds) were then sown on ½ MS medium and left for 7/8 days in a growing chamber at 25° C. On the day before transformation (D−1), the *Agrobacterium* culture was made as follows: 10 ml of liquid LB+antibiotics depending on plasmid/bacteria resistance was innoculated with a bacterial colony or glycerol stock, followed by incubation for 24 h to 48 h at 28° C. with shaking (250 rpm). Cotyledons were prepared the same day by cutting them at both extremities and temporarily putting into KCMS. The cut cotyledons were then recovered and laid on solid KCMS Petri dishes (upper face on the medium). The petri dishes were then placed in the dark at 25° C. in growing chamber for 24 h.

On the day of transformation (day D), the Agrobacteria suspension was centrifuged for 10 min at 3000 rpm. The bacterial pellet was then resuspended in liquid KCMS to an optical density close to 1. The culture was then diluted in a sterile falcon tube to an optical density between 0.05 and 0.08 (final volume of 30 mL). For transformation, the cotyledons were collected from the KCMS plate and soaked in the bacterial suspension (0.05-0.08 OD) for 30 min with shaking. The cotyledons were then dried on sterile Whatman paper (sterile Kleenex) and laid again on the petri dish with solid KCMS. Petri dishes are incubated in the dark for 48 h in growing chamber at 25° C.

Two days after transformation (day D+2), the cotyledons were laid on 2Z medium with 400 mg/L of Augmentin (Co-amoxiclav)+Kanamycin 75 mg/L for 15 days for plantlets regeneration. The medium was changed every 15 days or more frequently in case of contamination. Usually the concentration of Augmentin was reduced to 200 mg/L (or to 400 mg/L in the case of agro development). 38 independent transgenic plants were selected by Kanamycin. When plantlets were well developed, they were picked on rooting medium until their acclimatization in the greenhouse.

Media Components

TABLE 1

|  | liquid KCMS | solid KCMS | 2Z | Rooting medium | MS 1/2 |
| --- | --- | --- | --- | --- | --- |
| Volume | 1 l | 1 l | 1 l | 1 l | 1 l |
| MS (Basal salt, Duchefa MO221) |  |  |  | 2.2 g |  |
| MS (Including vitamins, Duchefa, MO222) | 4.4 g | 4.4 g | 4.4 g |  | 2.2 g |
| Sucrose | 20 g | 20 g | 30 g | 10 g | 15 g |
| KH$_2$PO$_4$ | 200 mg | 200 mg |  |  |  |
| pH | 5.8 | 5.7 | 5.8 | 5.8 | 5.9 |
| Agar |  | 8 g | 8 g | 7 g | 8 g |
|  | Autoclaving | Autoclaving | Autoclaving | Autoclaving | Autoclaving |
| Thiamine | 0.9 mg/l | 0.9 mg/l |  |  |  |
| Acetosyringone | 100 µM | 100 µM |  |  |  |
| 2.4D | 200 µg/l |  |  |  |  |
| Kinetin | 100 µg/l |  |  |  |  |
| R3 vitamins |  |  |  |  | 500 µl |
| Nitsch vitamins x1000 |  |  | 1 ml | 1 ml |  |
| Zeatin Ribosid |  |  | 2 mg/l |  |  |
| IAA |  |  | 0.87 mg/l |  |  |
| Kanamycine |  |  | 75 mg/l | 50 mg/l |  |
| Augmentin |  |  | 400 mg/l then 200 mg/l | 200 mg/l |  |

The composition of R3 Vitamins were as follows: thiamine 1 g/l, nicotinic acid 0.5 g/l and pyridoxine 0.5 g/l. The composition of Nitsch Vitamins were as follows: biotin 0.05 mg/l, folic acid 0.5 mg/l, glycine 2 mg/l, myo-inositol 100 mg/l, nicotinic acid 5 mg/l, pyridoxine HCl 0.5 mg/l and thiamine HCl 0.5 mg/l.

T-DNA insertion into the plant Micro-Tom genome was confirmed by PCR analysis for the presence of the nptII gene, which confers kanamycin resistance during tissue culture (data not shown). PCR analysis was performed using a Phire® Plant Direct PCR Kit with primers npt II-Forward (5'-CACCATGATATTCGGCAAGCAG-3') (SEQ ID NO:6)

and npt II-Reverse (5'-TGTGCTCGACGTTGTCACT-GAA-3') (SEQ ID NO:7) using the following components and conditions:

| | |
|---|---|
| 2x Phusion ® Master Mix | 10 μl |
| 5930-5F (10 μmol/L) | 0.5 μl |
| 5930-5R (10 μmol/L) | 0.5 μl |
| Phire ® Hot Start DNA Polymerase | 0.4 μl |
| Leaf samples | 0.5 mm |
| ddH2O | Up to 20 μl |
| 98° C. | 5 min |
| 98° C. | 5 sec |
| 60° C. | 5 sec |
| 72° C. | 20 sec |
| 40 cycles | |
| 72° C. | 1 min |

Example 4

QPCR Analysis in Tomato

Expression of Le005930 was measured relative to a housekeeping gene, in this case an elongation factor (GenBank accession number: X14449). QPCR analysis was performed on wild type fruit (Alisa Craig) and transgenics (large tomato). The housekeeping gene LeELF-α was used as a control (GenBank accession number: X14449). The following primers were used in the analysis of LeELF-α and Le5930 levels:

```
LeELF-F:
                                    (SEQ ID NO: 8)
5'-ACCTTTGCTGAATACCCTCCATTG-3'

LeELF-R:
                                    (SEQ ID NO: 9)
5'-CACACTTCACTTCCCCTTCTTCTG-3'

LeELF-probe:
                                    (SEQ ID NO: 10)
(FAM)5'-TCGTTTTGCTGTGAGGGACATGAGGCA-3' (TAMARA)

5930-Q-F:
                                    (SEQ ID NO: 11)
5'-TTGCCCCAGGTGGTCAGTTCTAT -3'

5930-Q-R:
                                    (SEQ ID NO: 12)
5'-CAGTGCCAAGTCTCTGCAGGTTT -3'

5930-Q-Probe:
                                    (SEQ ID NO: 13)
(FAM)5'-ATCCGAACGGTTTACAAGTGTGGGGTT-3' (TAMARA)
```

Reaction Components and Conditions:

| | |
|---|---|
| 2x Taqman Universal PCR Mastermix | 7.5 μl |
| F-Primer (10 μmol/L) | 0.45 μl |
| R-Primer (10 μmol/L) | 0.45 μl |
| Probe (10 μmol/L) | 0.3 μl |
| cDNA | 5.0 μl |
| Water (molecular grade) | 1.3 μl |
| Final Volume | 15 μl |
| 95° C. | 10 min |
| 95° C. | 10 sec |
| 60° C. | 50 sec |
| 72° C. | 1 sec |
| 45 cycles | |
| 40° C. | 10 min |

These results demonstrate that the Le005930 gene was significantly increased in expression in comparison to WT in the 3 selected transgenic lines at the immature green, mature green and breaker stages of fruit development.

Example 5

Tomato Colour Index Measurements

Figure 3:
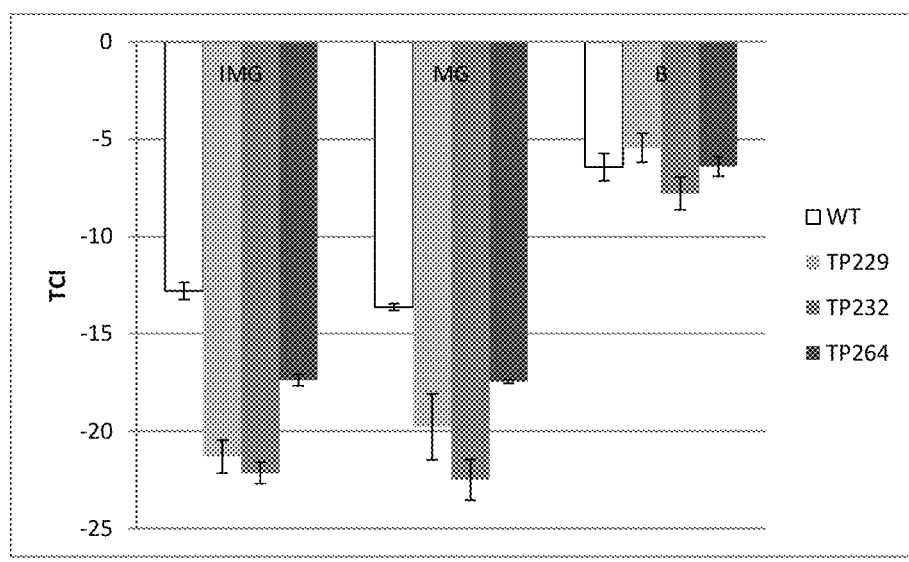
FIG. 3 Tomato colour index data for lines overexpressing Le5390 at different stages of development compared with wild type. Abbreviations same as for FIG. 2.
Figure 7:
FIG. 7 Photographs representing tomato fruit overexpressing Le5930 (TP232) and wild type fruit at the A) immature green stage B) mature green stage and C) breaker stage. TP232 fruit and wild type fruit are shown on the left and right of each photo respectively.
Figure 7:
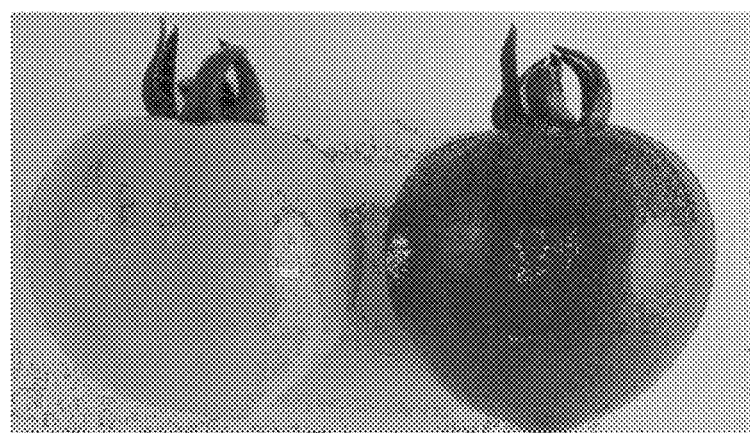
Figure 7:
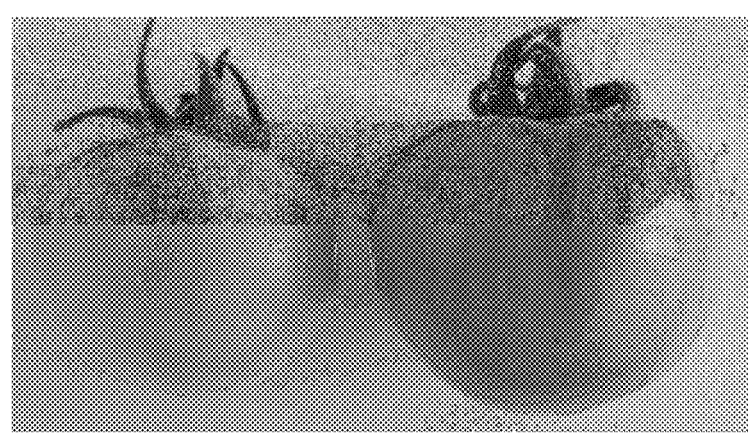

Tomato colour index (TCI) measurements were made using a MINOLTA colour measure machine to obtain 3 colour parameters L, a and b. For calculating TCI the following formula was used: $(2000a)/(L*(a^2+b^2)0.5)$. The TCI results show that the colour of the fruit of plants overexpressing Le005930 are significantly darker than wild type fruits at the immature growth stage (FIG. 3). This can be visualised in a separate experiment comparing TP232 line overexpressing Le005930 against wild type tomato at different growth stages (FIG. 7).

Example 6

Tomato Texture Testing

Figure 4:
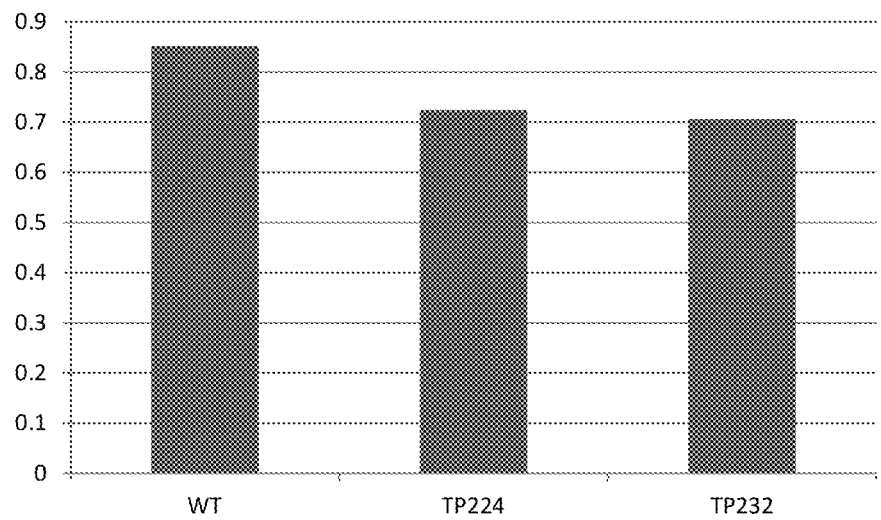
FIG. 4 Tomato texture test data for A) fruits overexpressing Le5930 and B) RNAi Le5930 fruits compared with wild type at the mature green stage.
Figure 4:
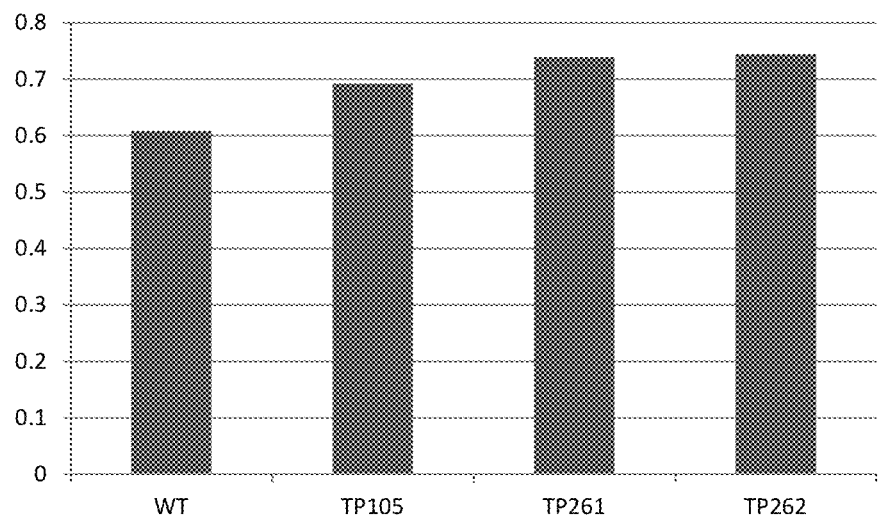

The texture tests were performed using a Stable MicroSystems Texture Test Machine. A 2 mm diameter probe was allowed to come into contact with the fruit surface at 5 mm/s and the force required to depress the fruit surface for 2 mm was recorded. The results showed that fruit overexpressing Le005930 had a texture phenotype consistent with having improved ripening properties (FIG. 4A). On the other hand, RNAi fruit which did not express Le005930 had decreased ripening (FIG. 4B).

Example 7

Chlorophyll Measurements in Tomato

Figure 5:
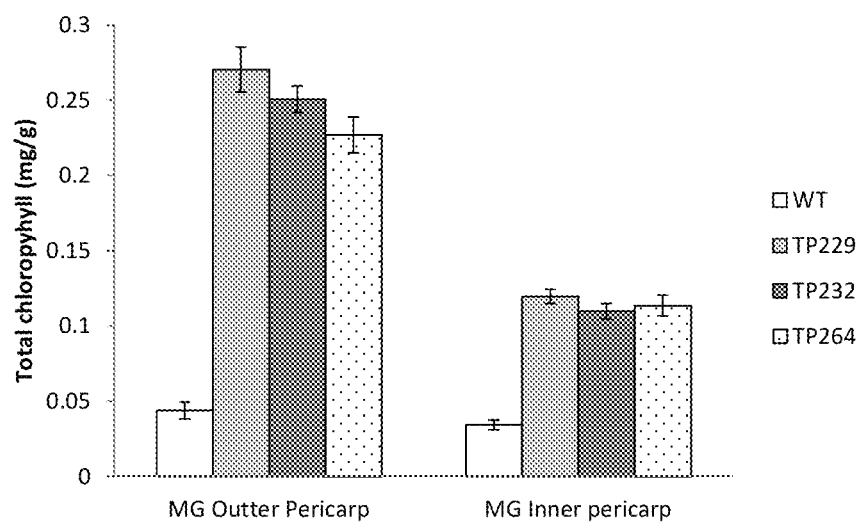
FIG. 5 Total chlorophyll content data in the outer and inner pericarp for tomato lines overexpressing Le5930 at the mature green development stage compared with wild type.
Figure 6:
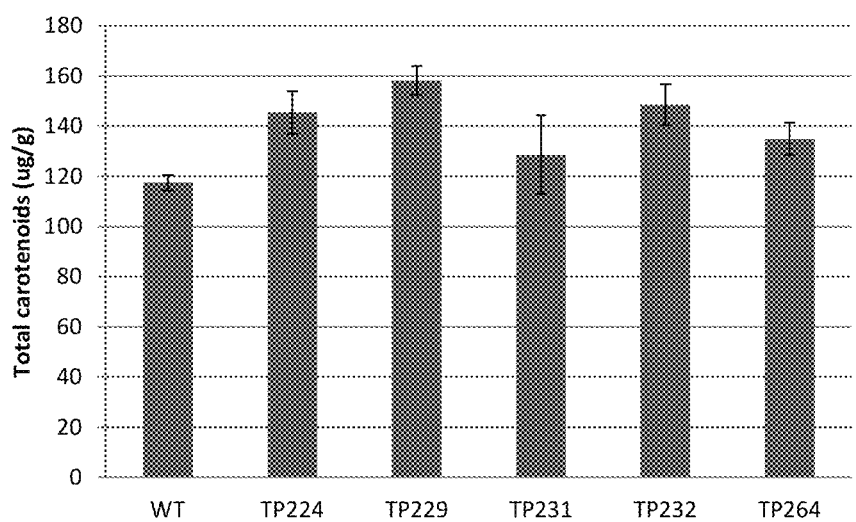
FIG. 6 Total carotenoid content data for Le5930 overexpression tomato lines TP224, TP229, TP231, TP232 and TP264 compared with wild type.

For chlorophyll measurements, a section of the epidermis and pericarp was cut from an area above a locule in a 5 mm wide strip around the equator of mature green and ripe fruit, weighed and ground in a pestle and mortar with acid washed sand (Sigma-Aldrich Company Ltd, UK) and a few ml of 60:40% hexane:acetone. The hexane:acetone was removed and stored in a glass universal bottle wrapped in foil, and replaced repeatedly with fresh liquid until no longer discoloured by grinding of the fruit. The optical absorbance of the samples was immediately measured in a Phillips PU 8720 scanning spectrophotometer and the chlorophyll and carotenoid contents were calculated with the following equations: total chlorophyll mg ml_1=8.02 (OD663)+20.2 (OD645) and total carotenoid mg ml_1=(OD450)/0.25 (Fray and Grierson, 1993). Individual tissue samples were taken from 1-3 fruit for each line (Forth & Pyke, 2006). Results show that lines overexpressing Le005930 have more chlorophyll when mature green (TP229, TP232 and TP264) and which accounts for the darker colour of the overexpression lines—see FIG. 5, whereas the RNAi line (TP262) has much less when compared with wild type fruit (data not shown).

Example 8

Tomato Fruit Plastid Counting

To obtain single cells, tomato fruit outer and inner pericarp (1 mm$^2$ sections) cells were separated and fixed immediately after excision with a sterile razor blade in 3.5% glutaraldehyde solution for one hour in darkness. Green fruits was disrupted as described previously and as follows: Heat-treated at 65° C. in a solution of disodium ethylenediaminetetraactic acid (0.1M, pH9.0) for up to 20 min followed by maceration with clean forceps on glass microscope slides (Pyke and Leech, 1991). Ripe-fruit pericarp was disrupted in a solution of disodium ethylenediaminetetraactic acid (0.1M, pH9.0) at room temperature. Tissue was stored at 4° C. in EDTA-Na2 solution for up to six months. For plastid counting, single cells from outer or inner pericarp were fixed on the slice. Plastids counting under Leica (CTR5000) microscope under object lens 20×. Plastid number in the outer pericarp was significantly higher in the Le005930 gene overexpressing lines compared with wild type ($p<0.001$).

Example 9

Tomato Chloroplast Size Analysis

One thick 1 cm3 hand cut section was removed from the mid point of each fresh glasshouse grown pepper fruit. Each section was mounted in water on a glass microscope slide and covered with a glass coverslip. Chloroplasts were visualised within each section using a BioRad Radiance 2100 laser scanning confocal microscope. The following settings were used: 488 nm Argon ion laser line, 50% power, ×40 objective, 1024×1024 resolution, no zoom, 50 lps scan speed. Three random fields of view were imaged within each section i.e. 3 fields of view per fruit were captured. Images were exported as TIFs and the size of chloroplasts was analysed in Image J. For both TP (overexpressor) and WT (wild type) lines, chloroplasts located in the inner pericarp appeared to be bigger than those located in outer pericarp tissue. There was no easily observable size differences between chloroplasts present in the inner pericarp of TP versus WT lines. Chloroplasts located in the outer pericarp tissues of TP lines appeared to be larger than chloroplasts located in the outer pericarp tissues of the WT.

Example 10

Expression Profiling of Pepper Gene Transcripts

Figure 8:
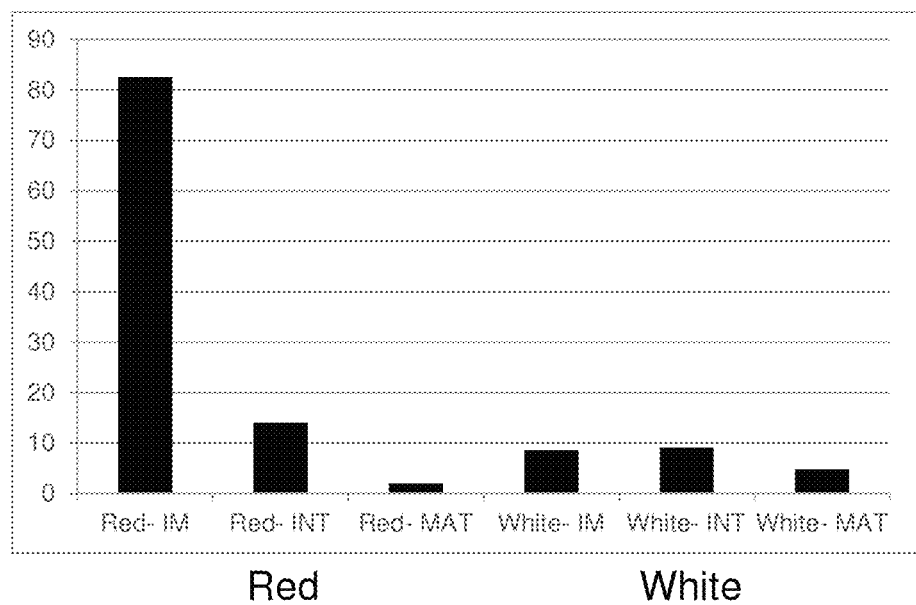
FIG. 8 A) Expression profiling of APRR2 like gene in red and white fruited parent pepper lines and B) sum of all chlorophyll binding protein transcripts.
Figure 8:
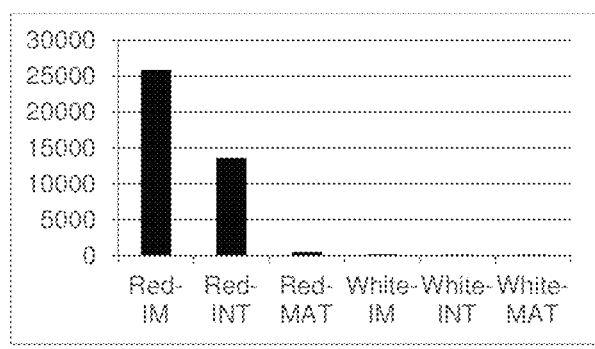

A white pepper parent was obtained from Paul Bosland, University of New Mexico. The red pepper parent was developed internally by Syngenta. A pilot experiment was performed using mRNA sequence. Samples were field grown pepper plants, and samples were pooled from 3 replicates. The results indicate that the relative transcript abundance of pepper APRR2 like mRNA is high at the immature stage in the red parent, but low in the white parent at the same stage (FIG. 8a). The sum of all chlorophyll a/b binding protein transcripts was also measured. The sum of all those detected (28 in total) indicates that APRR2 like expression mirrors the expression of the chlorophyll machinery. (FIG. 8b).

Example 11

Generation and Analysis of a G-A Substitution Responsible for Protein Truncation in the Pepper APRR2 Like Gene To find the pepper APRR2 homologue a tomato EST sequence (SGN-U585565) was used to BLAST a pepper EST database. The best hit with 90% homology over 263 bases was KS19056805. Because this EST was only a partial sequence and also appeared to be chimeric, a P32 probe was made from the 3' end of the EST sequence using the primers 5' GGTTTACAAGTGTGGGGTTCACC 3' (SEQ ID NO: 17) and 5' CATCGAATGACTTCTCTAGCATGCTA 3' (SEQ ID NO: 18) using an Amersham Rediprime II labeling kit. A *Capsicum frutescens* (cv BG2816) BAC library filter from Cornell University was hybridized with the probe using standard hybridization protocols found on the Clemson University Genomics Institute website. BAC 85L18 was recovered from the library screen and sequenced using primer walking with an ABI3730XL sequencer.

The genomic wild type pepper APRR2 sequence generated was as follows (SEQ ID NO: 14):

>1553
TTTCCCCTAAAAAAGATCTATTACATGGGGTTTTTCTGTTTTATGTTGG
TTCTTATTTAAAGCTGAAAATAGTCTTTGTCTCTTTCCTTTTTGTTAGA
TGATGTTGAAGATTCAAGCTTGAAAAAGTGTGTCAGAAGGAGTGGGGGGG
GGGGGGGTTGATTTTTTTTGTTTATTTTGAGACATGTACTATTATTATGA
GTGATATTTACTGTAAGGTTTAAGAGGGATTTTGCTAAAGGTTGAATTTT
TAATGTAAATCTGAGGGGAATTCCTTTTTGGATGTGCAGATTCAATTGGT
AATGACTGATTAAGTGACTGTTTTTGGAGGCACTAATTTGGCTGACCTAA
AAAGGATGCCTTTTTAGAAATGATTTGCATTGAGGATGAATTATTGGGTT
GGAAAGATTTCCCAAAGGGGCTTAAAGTCCTCCTCCTTGATGAAGATAGC
AGCTCTGCTGCTGAGATGAAATCAAGGCTTGAGAAAATGGACTATATAGG
TAAGTAGTTGTAACCCAGTCTAAAAATACTTACTCGCACCCGGTGTTTAT
GTTTTTTTTTTTCTTTTGGTTTTGCTCATTCCTTTTGGTGTTGCCTGTA
AAGTTGCTGCAATATGACTAGGAGGTCAGAAACAGCCTCTTGCTGAAATG
CAAGGTAAGGCTGCGTACAATAAACTCATGTAGTTCGACACTTTCCTATG
CATATCGGGAGTTTTGGTGCACGGGCTGCCCTCATCCCTTTTGGTACAA
AATTTTTTGGTTTAGTCACTTTCTGTTTTGCAAGTTAGTTGTGCATTTCT
TGGTCTGTTTCTTTGTTGATTTCTCCTTATATAGAAGTTCCTTTACATTT
ATTACTTAGGGAAAATAGAGTATTCTGATTCATCTTTTCTATTTTAAGAC
AAAACATTTAAGTGGTTCAGGATTCATACTTCTACCTTTTCCTGGAATGC
TGCAGAGGTCCTCTAACAAGATAGAATTTGAACTTCCCTTTATGGTTCTT
GCAAGTTTATACTCCCTCGGTTTCAATTTGTTTGTCTGGCCTTGACTCAG
GGGCGGACCTACATGGTCCATGCCGGGTGCTTGAGCAACCAATGACCCCT
CAAGTGATGTGGATTCGATTCCTGGTAGCAACACTTTTTTTTCGTAAAGG
AATTGAGCACCCACAACCTTCAAATCCTGGATCCGCGCTGCTTTGACTTG
ACACGAAGTTTAAGAAAGTAAATGAGTCTGAATCTTGTGGTCTTAAACTA
AAGATAAGCTAAAACAAATAAATTGAAACTGAGGGAATATCTATTTATGA
TGTTTCAAAATTTGGGTTAATTAGTTGCTTCACATTAGCAGATATTGAAT
GATTCACTGTTGAATGCTCTGAATTACCGTAGTTATCAAATTTGTTTTTC
ATTCTTTCTTTAACCTTTGAAGTAATGTGACTAGCGGAATATAGTTTCTT
TGAAGCAACAACTTATTTTATGATTAGGATGACATTTTGCTCAGTCCTTA
GCTTGTTTTTTTTCCACAAAATTGTTCTTGAATTTGTTTCATTTCGCGGA

TCTTCCTGAAAGGTCATTATTATATTCATATGCTATAAACCCACCATGTA
ATTGCAGTCTACACGTTCTGCAATGAGAGTGAAGCTTTGTCTGCAATCTC
TAGCAAATCCGAGGGCTTTCATGTTGCCATTGTGGAGGTAGTAGTTACAT
TTTTACTTGAAACTTTCCATATTCACCTTTATGGTAAGACTATTGATCAA
CAAAATATATTGATCAACAAAATATGAAGACAGGCCAGAATGTTATTCTA
ACTGTTGATGAATTTGTCTATCAATTGACACAGGTAAGTGCAGGCGATAA
TGATGGGGTCCTCCAATTTCTTGAAAGTGCCAAAAATCTACCAACTATAA
GTGAGTGCTATATATACGAAAAAATAAGTGGCGTATTGCAAGTTGACTTA
GTTTCAGCAGATATGATAGTATTGGCAGAGTTAGAAGTGCTAGAATCTTA
AGTCTTCCAACTATCACGTAGACCACTGAACTTGGAATATTTTGCTTGTC
TTCAAATGTTTAAACGCTATAACATATCTAAGGGAGCTTTGTTTACTTCG
TGCAGTGACATCAAATATTCATTCTCTCAGCACAATGATGAAGTGTATTG
CGGTGAACTCTTGGGCTCAAATTTTCATTTGATGCTAACTGTTTCTGGT
AATTATGTGTGAAAGATGTTCAATGCTTCGATATTTTGCAGCTTGGTGCA
GTTGAGTTCCTTCAGAAACCATTATCAGATGACAAACTCAAAAATATATG
GCAGCATGTAGTTCACAAGGTTTGTAATCCAAACTTCACACAATCAGCTT
AGTTCTTTCAAATCAGTATGCTTATTATATGAAAAGGAAATCCTGATCTT
ATTGGTTGCAACAGGCATTCAATGCTAGAAAGGATGTGTCCGGACCACTT
GAGCCGGTAAAAGAATCTCTTCTTTCGATGCTACAGCTACAACCAGAAAA
GGGTGAACCAGATGACAAAAGTTCAAATGAACAGAACCTCTCATTGCAG
TTGCGGACAACAATACCGAACAGTCATCGGGCTGTGATAAATACCCTGCT
CCCTCAACCCCTCAATTGAAACAAGGAGTGCGGTCAGTGGATGATAGTGA
CTGCCATGATCATACTATCTTCTCAACTGACCAAGACAATGGGGAGCATG
ATGGTGACACTAAATCCGTCGAAACTACTTATAACAATTCACTTGCTGAG
AATACTGTCCAAATAAGTCCTCCTGGGCAACAAGAAGATATAATTTTGAA
AGAGGAGAATGGTTCATCTCCTCATCAAACTATGGAGGCTGATATTGCTA
CCTTTTCACAAATTAATGACTGCGCTGACAATAGTGATGGTTCATCTCCT
CATCAAAAGACGGAGGCTGATATTGCTACTACCTCTTCACAAAGTAAAGA
CTGCCCTGACAATAGCATTAGTCATTCTGCTGAACCTAGTAAAGCTTCTG
GTCCCCATAGCTCAAGTGGGACTAAATCCAATAAGAAAAAGGTGAAGGTA
AGATGGAAGAAATGATACTTTGGTTCTCATAGTACAATAATGAAGTAACT
ACGCACTCAACGGTCCGTAATATTAGTGTCCAAGAATGCCATTATGTTTT
GTCTACTGGTTCCGAAGGTATAAGAATGTTGCATAACTTTCGCATGCATT
CTTAAAACATGTTTCATGATTGCTTCTCTTGCTCATCAGTCATACGGTCT
TTTGTTATTTATCTCTTCTTTCTATAAAAGGGGATGAGATGAAGATATTA
CATGTGGCATTGCGTGTATCTTTCTCCTCTTGCATTAACGAATTTAGCCT
TATGAACTGTTAAGTTCTTAGAGAACTTCATGGCTATCATAGAACATCCT
TTTCAAGTTCCATTTCGTCTATGATTTATCAATTACAGTGGATCTTTCAA
GATTCTGCTTAAAGCACCTTTAAGATGAATGCGAGGCTCATTTTGTTATC
TCGAAGTTTGAACTTCTCAAACGGTGTATGAATCTATAATATGGTAATCA
GTATAGGAATTTAGCTAGAGTTGTGTTGGGGATTTCAGCCTTAAATGTAG
TTGACTGAGCAGCGGTGAAACAATTCTGCATTCTTCGAAGTTTGAATTGC
GTGTTTCAGGGGGATAAGTTTGGTATTTCCTTTGGATTCAGGTAGATTGG
ACACCTGAACTACACAAAAAGTTTGTTCAAGCAGTAGAGCAACTCGGTAT
AGATCAAGCCATTCCTTCTCGAATACTAGACGTGATGAAAGTGGAGGGCT
TAACGAGACATAACATAGCTAGCCATCTCCAGGTTTGTGAGTTCTGCTCT
TTCATATCTTAATGAATATGTTTGCTATGTTTGGCAGCGTCGGAAGCAAT
TTGGCTGAAAGATGTCTTAATATAAATGTTCTAACATTGGGGAAAACGCG
ATAGTACTAAATCTTGACCATTTTCAGCCTGTTGGCACCTCAAGTTAGAT
AAATATTCATTTGATATTTCCATATCCTTGGAGGGGATGTAGTATAGCAG
TTGTGCTACAAAAAAGTTGGATGTTGATAATATTTTTCCGTTTAACAATA
GTATCACCTTTCAATTTCCAAGCAGAAATACAGAATGCATCGGAGGCAAA
TTTTGCCAAGGGAAGTGGAAAGGAGATGGCCCCATCCGCAACCTAGAGAT
TCAGTACAAAGGAATTACTATCCTCATAAACCTGTCATGACATTCCCACC
ATATCATTCTAATCATGTCGCCCCAGCTGGTCAATGTTATCCTGCTTGGG
TACCACCGGCTAGTTATCCGAATGGTTTACAAGTGTGGGGTTCACCTTAC
TATCCGGGATGGCAGCCTGCAGAGACTTGGCACTGGAAGCCTCATCCAGG
GGTAAACCTTTTTTTCCCTTAGACCACATTGCATGCCTATGTCAACATAT
TTCACAGGATATTTTAGGTCTAGGAAATACCACACCTAAAAACTTATGTT
TTGTAATAATGCAGCTGCTTGCTGATACATGGGGCTCCCCTGTCATGCCA
CCATCGTTTGGATCGTATCCACCATATCCCCAGGTGAGTTCATTGGCAAT
ATATCACCCCCGTTAGATATTTTTATGTTCAATATGACAACGTTCTTGAG
ATATTTCATGTGAATGCACTCTTGGGTTGAGTTCTTAATGGCACATCGGT
TGGATGATGCAGAATGCTGGAATGTACCAGTCTCACGGAATGCATAACAG
ATATAGCATGCTAGAGAAGTCATTCGATGTTCACCCGGTAAGATTGTAGA
TCCTATTTCAGACCGACAAACTTCTTTATACATAAATGCACTAGGAGATT
ATTCATATTCCAGTTTCGTTTTCCCTTTTGGAGCTACAAAGGAAAAACAC
AACGTAAATGTTTTATGGCTTATGTTGTATTAAGTGAAGGAAAATGTTTT
TCAATTTTTCGATGTTCCACTGGTCAAAAGTTTTGAAAAATATTTTCTCT
AGAAAAATAAGTTGCTTGAAAAATGAGAAAAATGACATTTCTAGTGGAAG
TAAGGAAAACAAGTTCCACCTGTGGCATTCCACATTGATTGTGTTCTCAT
TCCTCCCAATACTCCAACACACTTCATCTTCACCCCTACCCTCGTAGCTC
CATGCCCACCGTCCATAATATTCTCTAGATTATACAAATACTTTAAGG
ACAATGTTTTTTGTTTACGTGCCGAACACTAGAAAATAAGTAAGAACCG
AACATAAGAAAGTACGTTTCTAAGTAAGAAACTCACTCATTTTCCTAGAA
AATATTTTCCACGAAAACATTGTTCGTGGAAAACATTTTCCTTCATACCA
AACACACCCTTAGCCCTAGAATTCATTCGATAATCGTGCCAAAACTACAT
ATGTGTAATGAAGGGGAGGCACTGGGTTAAACTTGACCAATCATCTCCAA
AATGGATCTAAATTACATACAATACAACTACACTGCTAACGTACTCAGTG
CAATCTCATGAGTGGCTAAATTACATACAATCACCGGGTAAAAAGAGAAT

-continued

ATATTATTTGACTAGTATGTATAATTAGTTGTCACATTGGTTTAAGAAGG
GGTTATAGTGTCTTGGACAACCCTTACCATGCTAGCTTTTGAGGTTTGAT
TAGGCCTAAGGTCCATTTTATCATAACTAGATTATCGACCCCCACCCCCC
CGGTACACTATAGCTAGTATTGGTCTCCTAGTAACTTGATAGTATAAAT
TTTTTATTGGTTAAGTTTTGGTTGGTGGTGTGTGCAG

From this, pepper APRR2 cDNA sequence can be predicted (SEQ ID NO: 2):

```
>1553CDS
atgatttgcattgaggatgaattattgggttggaaagatttcccaaggggcttaaagtcctcctccttg
atgaagatagcagctctgctgctgagatgaaatcaaggcttgagaaaatggactatatagtctacacgtt
ctgcaatgagagtgaagctttgtctgcaatctctagcaaatccgagggctttcatgttgccattgtggag
gtaagtgcaggcgataatgatgggtcctccaatttcttgaaagtgccaaaaatctaccaactataatga
catcaaatattcattctctcagcacaatgatgaagtgtattgcgcttggtgcagttgagttccttcagaa
accattatcagatgacaaactcaaaaatatatggcagcatgtagttcacaaggcattcaatgctagaaag
gatgtgtccggaccacttgagccggtaaaagaatctcttctttcgatgctacagctacaaccagaaagg
gtgaaccagatgacaaaagttcaaatggaacagaacctctcattgcagttgcggacaacaataccgaaca
gtcatcgggctgtgataaataccctgctccctcaacccctcaattgaaacaaggagtgcggtcagtggat
gatagtgactgccatgatcatactatcttctcaactgaccaagacaatggggagcatgatggtgacacta
aatccgtcgaaactacttataacaattcacttgctgagaatactgtccaaataagtcctcctgggcaaca
agaagatataattttgaaagaggagaatggttcatctcctcatcaaactatggaggctgatattactacc
tcttcacaaagtaaagactgccctgacaatagcattagtcattctgctgaacctagtaaagcttctggtc
cccatagctcaagtgggactaaatccaataagaaaaaggtgaaggtagattggacacctgaactacacaa
aaagtttgttcaagcagtagagcaactcggtatagatcaagccattccttctcgaatactagacgtgatg
aaagtggagggcttaacgagacataacatagctagccatctccagaaatacagaatgcatcggaggcaaa
ttttgccaagggaagtggaaggagatggcccatccgcaacctagagattcagtacaaggaattacta
tcctcataaacctgtcatgacattcccaccatatcattctaatcatgtcgccccagctggtcaatgttat
cctgcttgggtaccaccggctagttatccgaatggtttacaagtgtggggttcaccttactatccgggat
ggcagcctgcagagacttggcactggaagcctcatccagggctgcttgctgatacatgggctcccctgt
catgccaccatcgtttggatcgtatccaccatatccccagaatgctggaatgtaccagtctcacggaatg
cataacagatatagcatgctagagaagtcattcgatgttcacccg
```

The truncated pepper APRR2 cDNA sequence comprises the following sequence (SEQ ID NO: 15):

```
>16113CDS
atgatttgcattgaggatgaattattgggttggaaagatttcccaaggggcttaaagtcctcctccttg
atgaagatagcagctctgctgctgagatgaaatcaaggcttgagaaaatggactatatagtctacacgtt
ctgcaatgagagtgaagctttgtctgcaatctctagcaaatccgagggctttcatgttgccattgtggag
gtaagtgcaggcgataatgatgggtcctccaatttcttgaaagtgccaaaaatctaccaactataatga
catcaaatattcattctctcagcacaatgatgaagtgtattgcgcttggtgcagttgagttccttcagaa
accattatcagatgacaaactcaaaaatatatggcagcatgtagttcacaaggcattcaatgctagaaag
gatgtgtccggaccacttgagccggtaaaagaatctcttctttcgatgctacagctacaaccagaaagg
gtgaaccagatgacaaaagttcaaatggaacagaacctctcattgcagttgcggacaacaataccgaaca
gtcatcgggctgtgataaataccctgctccctcaacccctcaattgaaacaaggagtgcggtcagtggat
gatagtgactgccatgatcatactatcttctcaactgaccaagacaatggggagcatgatggtgacacta
```

-continued

```
aatccgtcgaaactacttataacaattcacttgctgagaatactgtccaaataagtcctcctgggcaaca
agaagatataattttgaaagaggagaatggttcatctcctcatcaaactatggaggctgatattactacc
tcttcacaaagtaaagactgccctgacaatagcattagtcattctgctgaacctagtaaagcttctggtc
cccatagctcaagtgggactaaatccaataagaaaaaggtgaaggtagattggacacctgaactacacaa
aaagtttgttcaagcagtagagcaactcggtatagatcaagccattccttctcgaatactagacgtgatg
aaagtggagggcttaacgagacataacatagctagccatctccagaaatacagaatgcatcggaggcaaa
ttttgccaagggaagtggaaaggagatggccccatccgcaacctagagattcagtacaaaggaattacta
tcctcataaacctgtcatgacattcccaccatatcattctaatcatgtcgcccagctggtcaatgttat
cctgcttgggtaccaccggctagttatccgaatggtttacaagtgtggggttcaccttactatccgggat
ggcagcctgcagagacttgacactggaagcctcatccagggctgcttgctgatacatggggctcccctgt
catgccaccatcgtttggatcgtatccaccatatcccagaatgctggaatgtaccagtctcacggaatg
cataacagatatagcatgctagagaagtcattcgatgttcacccg
```

Truncated pepper APRR2 genomic sequence is as follows (SEQ ID NO: 16):

```
>16113
TTTCCCCTAAAAAAGATCTATTACATGGGGTTTTTTCTGTTTTATGTTGG
TTCTTATTTAAAGCTGAAAATAGTCTTTGTCTCTTTCCTTTTTTGTTAGA
TGATGTTGAAGATTCAAGCTTGAAAAAGTGTGTCAGAAGGAGTGGGGGGG
GGGGGGTTGATTTTTTTTGTTTATTTTGAGACATGTACTATTATTATGAG
TGATATTTACTGTAAGGTTTAAGAGGGATTTTGCTAAAGGTTGAATTTTT
AATGTAAATCTGAGGGGAATTCCTTTTTGGATGTGCAGATTCAATTGGTA
ATGACTGATTAAGTGACTGTTTTTGGAGGCACTAATTTGGCTGACCTAAA
AAGGATGCCTTTTTAGAAATGATTTGCATTGAGGATGAATTATTGGGTTG
GAAAGATTTCCCAAAGGGGCTTAAAGTCCTCCTCCTTGATGAAGATAGCA
GCTCTGCTGCTGAGATGAAATCAAGGCTTGAGAAAATGGACTATATAGGT
AAGTAGTTGTAACCCAGTCTAAAAATACTTACTCGCACCCGGTGTTTATG
TTTTTTTTTTTTTCTTTTGGTTTTGCTCATTCCTTTTGGTGTTGCCTGTAA
AGTTGCTGCAATATGACTAGGAGGTCAGAAACAGCCTCTTGCTGAAATGC
AAGGTAAGGCTGCGTACAATAAACTCATGTAGTTCGACACTTTCCTATGC
ATATCGGGAGTTTTGGTGCACGGGGCTGCCCTCATCCCTTTTGGTACAAA
ATTTTTTGGTTTAGTCACTTTCTGTTTTGCAAGTTAGTTGTGCATTTCTT
GGTCTGTTTCTTTGTTGATTTCTCCTTATATAGAAGTTCCTTTACATTTA
TTACTTAGGGAAAATAGAGTATTCTGATTCATCTTTTCTATTTTAAGACA
AAACATTTAAGTGGTTCAGGATTCATACTTCTACCTTTTCCTGGAATGCT
GCAGAGGTCCTCTAACAAGATAGAATTTGAACTTCCCTTTATGGTTCTTG
CAAGTTTATACTCCCTCGGTTTCAATTTGTTTGTCTGGCCTTGACTCAGG
GGCGGACCTACATGGTCCATGCCGGGTGCTTGAGCAACCAATGACCCCTC
AAGTGATGTGGATTCGATTCCTGGTAGCAACACTTTTTTTTCGTAAAGGA
ATTGAGCACCCACAACCTTCAAATCCTGGATCCGCGCTGCTTTGACTTGA
CACGAAGTTTAAGAAAGTAAATGAGTCTGAATCTTGTGGTCTTAAACTAA
AGATAAGCTAAAACAAATAAATTGAAACTGAGGGAATATCTATTTATGAT
GTTTCAAAATTTGGGTTAATTAGTTGCTTCACATTAGCAGATATTGAATG
ATTCACTGTTGAATGCTCTGAATTACCGTAGTTATCAAATTTGTTTTTCA
TTCTTTCTTTAACCTTTGAAGTAATGTGACTAGCGGAATATAGTTTCTTT
GAAGCAACAACTTATTTTATGATTAGGATGACATTTTGCTCAGTCCTTAG
CTTGTTTTTTTTCCACAAAATTGTTCTTGAATTTGTTTCATTTCGCGGAT
CTTCCTGAAAGGTCATTATTATATTCATATGCTATAAACCCACCATGTAA
TTGCAGTCTACACGTTCTGCAATGAGAGTGAAGCTTTGTCTGCAATCTCT
AGCAAATCCGAGGGCTTTCATGTTGCCATTGTGGAGGTAGTAGTTACATT
TTTACTTGAAACTTTCCATATTCACCTTTATGGTAAGACTATTGATCAAC
AAAATATATTGATCAACAAAATATGAAGACAGGCCAGAATGTTATTCTAA
CTGTTGATGAATTTGTCTATCAATTGACACAGGTAAGTGCAGGCGATAAT
GATGGGGTCCTCCAATTTCTTGAAAGTGCCAAAAATCTACCAACTATAAG
TGAGTGCTATATATACGAAAAAATAAGTGGCGTATTGCAAGTTGACTTAG
TTTCAGCAGATATGATAGTATTGGCAGAGTTAGAAGTGCTAGAATCTTAA
GTCTTCCAACTATCACGTAGACCACTGAACTTGGAATATTTTGCTTGTCT
TCAAATGTTTAAACGCTATAACATATCTAAGGGAGCTTTGTTTACTTCGT
GCAGTGACATCAAATATTCATTCTCTCAGCACAATGATGAAGTGTATTGC
GGTGAACTCTTGGGCTCAAATTTTCATTTGATGCTAACTGTTTCTGGTA
ATTATGTGTGAAAGATGTTCAATGCTTTGATATTTTGCAGCTTGGTGCAG
TTGAGTTCCTTCAGAAACCATTATCAGATGACAAACTCAAAAATATATGG
CAGCATGTAGTTCACAAGGTTTGTAATCCAAACTTCACACAATCAGCTTA
GTTCTTTCAAATCAGTATGCTTATTATATGAAAAGGAAATCCTGATCTTA
TTGGTTGCAACAGGCATTCAATGCTAGAAAGGATGTGTCCGGACCACTTG
AGCCGGTAAAAGAATCTCTTCTTTCGATGCTACAGCTACAACCAGAAAAG
GGTGAACCAGATGACAAAAGTTCAAATGAACAGAACCTCTCATTGCAGT
TGCGGACAACAATACCGAACAGTCATCGGGCTGTGATAAATACCCTGCTC
```

-continued

```
CCTCAACCCCTCAATTGAAACAAGGAGTGCGGTCAGTGGATGATAGTGAC
TGCCATGATCATACTATCTTCTCAACTGACCAAGACAATGGGGAGCATGA
TGGTGACACTAAATCCGTCGAAACTACTTATAACAATTCACTTGCTGAGA
ATACTGTCCAAATAAGTCCTCCTGGGCAACAAGAAGATATAATTTTGAAA
GAGGAGAATGGTTCATCTCCTCATCAAACTATGGAGGCTGATATTGCTAC
CTTTTCACAAATTAATGACTGCGCTGACAATAGTGATGGTTCATCTCCTC
ATCAAAAGACGGAGGCTGATATTGCTACTACCTCTTCACAAAGTAAAGAC
TGCCCTGACAATAGCATTAGTCATTCTGCTGAACCTAGTAAAGCTTCTGG
TCCCCATAGCTCAAGTGGGACTAAATCCAATAAGAAAAAGGTGAAGGTAA
GATGGAAGAAATGATACTTTGGTTCTCATAGAACAATAATGAAGTAACTA
CGCACTCAACGTTCTGTAATATTATTGTCCAAGAATGCCATTATGTTTTG
TCTACTGGTTCCGAAGGTATAAGAATGTTGCATAACTTTCGCATGCATTC
TTAAAACATGTTTCATGATTGCTTCTCTTGCTCATCAGTCATACGGTCTT
TTGTTATTTATCTCTTCTTTCTATAAAAGGGGATGAGATGAAGATATTAC
ATGTGGCATTGCGTGTATCTTTCTCCTCTTGCATTAACGAATTTAGCCTT
ATGAACTGTTAAGTTCTTAGAGAACTTCATGGCTATCATAGAACATCCTT
TTCAAGTTCCATTTCGTCTATGATTTATCAATTACAGTGGATCTTTCAAG
ATTCTGCTTAAAGCACCTTTAAGATGAATGCGAGGCTCATTTTGTTATCT
CGAAGTTTGAACTTCTCAAACGGTGTATGAATCTATAATATGGTAATCAG
TATAGGAATTTAGCTAGAGTTGTGTTGGGGATTTCAGCCTTAAATGTAGT
TGACTGAGCAGCGGTGAAACAATTCTGCATTCTTCGAAGTTTGAATTGCG
TGTTTCAGGGGGATAAGTTTGGTATTTCCTTTGGATTCAGGTAGATTGGA
CACCTGAACTACACAAAAGTTTGTTCAAGCAGTAGAGCAACTCGGTATA
GATCAAGCCATTCCTTCTCGAATACTAGACGTGATGAAAGTGGAGGGCTT
AACGAGACATAACATAGCTAGCCATCTCCAGGTTTGTGAGTTCTGCTCTT
TCATATCTTAATGAATATGTTTGCTATGTTTGGCAGCGTCGGAAGCAATT
TGGCTGAAAGATGTCTTAATATAAATGTTCTAACATTGGGGAAAACGCGA
TAGTACTAAATCTTGACCATTTTCAGCCTGTTGGCACCTCAAGTTAGATA
AATATTCATTTGATATTTCCATATCCTTGGAGGGGATGTAGTATAGCAGT
TGTGCTACAAAAAAGTTGGATGTTGATAATATTTTTCCGTTTAACAATAG
TATCACCTTTCAATTTCCAAGCAGAAATACAGAATGCATCGGAGGCAAAT
TTTGCCAAGGGAAGTGGAAAGGAGATGGCCCCATCCGCAACCTAGAGATT
CAGTACAAAGGAATTACTATCCTCATAAACCTGTCATGACATTCCCACCA
TATCATTCTAATCATGTCGCCCCAGCTGGTCAATGTTATCCTGCTTGGGT
ACCACCGGCTAGTTATCCGAATGGTTTACAAGTGTGGGGTTCACCTTACT
ATCCGGGATGGCAGCCTGCAGAGACTTGACACTGGAAGCCTCATCCAGGG
GTAAACCTTTTTTTCCCTTAGACCACATTGCATGCCTATGTCAACATATT
TCACAGGATATTTTAGGTCTAGGAAATACCACACCTAAAAACTTATGTTT
TGTAATAATGCAGCTGCTTGCTGATACATGGGGCTCCCCTGTCATGCCAC
CATCGTTTGGATCGTATCCACCATATCCCCAGGTGAGTTCATTGGCAATA
TATCACCCCCGTTAGATATTTTTATGTTCAGTATGACAACGTTCTTGAGA
TATTTCATGTGAATGCACTCTTGGGTTGAGTTCTTAATGGCACATCGGTT
GGATGATGCAGAATGCTGGAATGTACCAGTCTCACGGAATGCATAACAGA
TATAGCATGCTAGAGAAGTCATTCGATGTTCACCCGGTAAGATTGTAGAT
CCTATTTCAGACCGACAAACTTCTTTATACATAAATGCACTAGGAGATTA
TTCATATTCCAGTTTCGTTTTCCCTTTTGGAGCTACAAAGGAAAAACACA
ACGTAAATGTTTTATGGCTTATGTTGTATTAAGTGAAGGAAAATGTTTTT
CAATTTTTCGATGTTCCACTGGTCAAAAGTTTTGAAAAATATTTTCTCTA
GAAAAATAAGTTGCTTGAAAAATGAGAAAAATGACATTTCTAGTGGAAGT
AAGGAAAACAAGTTCCACCTGTGGCATTCCACATTGATTGTGTTCTCATT
CCTCCCAATACTCCAACACACTTCATCTTCACCCCTACCCTCGTAGCTCC
ATGCCCACCGTCCATAATATTCTCTAGATTATATACAAATACTTTAAGGA
CAATGTTTTTTGTTTACGTGCCGAACACTAGAAAATAAGTAAGAACCGA
ACATAAGAAAGTACGTTTCTAAGTAAGAAACTCACTCATTTTCCTAGAAA
ATATTTTCCACGAAAACATTGTTCGTGGAAAACATTTTCCTTCATACCAA
ACACACCCTTAGCCCTAGAATTCATTCGATAATCGTGCCAAAACTACATA
TGTGTAATGAAGGGGAGGCACTGGGTTAAACTTGACCAATCATCTCCAAA
ATGGATCTAAATTACATACAATCAACAACACTACTAACGTACTCAGTGC
AATCTCATGAGTGGCTAAATTACATACAATCACCGGGTAAAAAGAGAATA
TATTATTTGACTAGTATGTATAATTAGTTGTCACATTGGTTTAAGAAGGG
GTTATAGTGTCTTGGACAACCCTTACCATGCTAGCTTTTGAGGTTTGATT
AGGCCTAAGGTCCATTTTATCATAACTAGATTATCGACCCCCACCCCCCC
GGTACACTATAGCTAGTATTGGTCTCCTAGTAACTTGATAGTATAAAATT
TTTTATTGGTTAAGTTTTGGTTG
```

Primers were designed to sequence the BAC. The BAC sequence was assembled using the Sequencher 4.9 assembly program from Genecodes Inc. To determine coding regions of the gene, the tomato and pepper EST sequences were subjected to BLAST analysis against the pepper genomic sequence using the BLAST2 algorithm. A map of the genomic sequence was generated using Vector NTI from Invitrogen.

To recover sequence from pepper lines 16113 and 1553A, DNA was extracted from young leaf tissue using the CTAB method (Doyle and Doyle, 1990). A subset of the primers above were then used to amplify regions of both pepper lines. The amplification products were Sanger sequenced on the ABI3730XL, and aligned using Sequencher.

Sequencing of the pepper APRR2 like gene from red and white fruited parents of the mapping population revealed evidence for a polymorphism between these 2 genotypes. By lining up the available cDNA sequence with the genomic sequence it was possible to identify a G-A substitution resulting in a stop codon in the white parent. Nucleotides 4218 to 4417 of SEQ ID NO: 14 are shown below. The translated amino acid sequence corresponds to SEQ ID NO:19. The codon containing the G-A substitution is highlighted; nucleotide 4379 of SEQ ID NO: 14 is a G, whereas nucleotide 4379 of SEQ ID NO: 16 is an A):

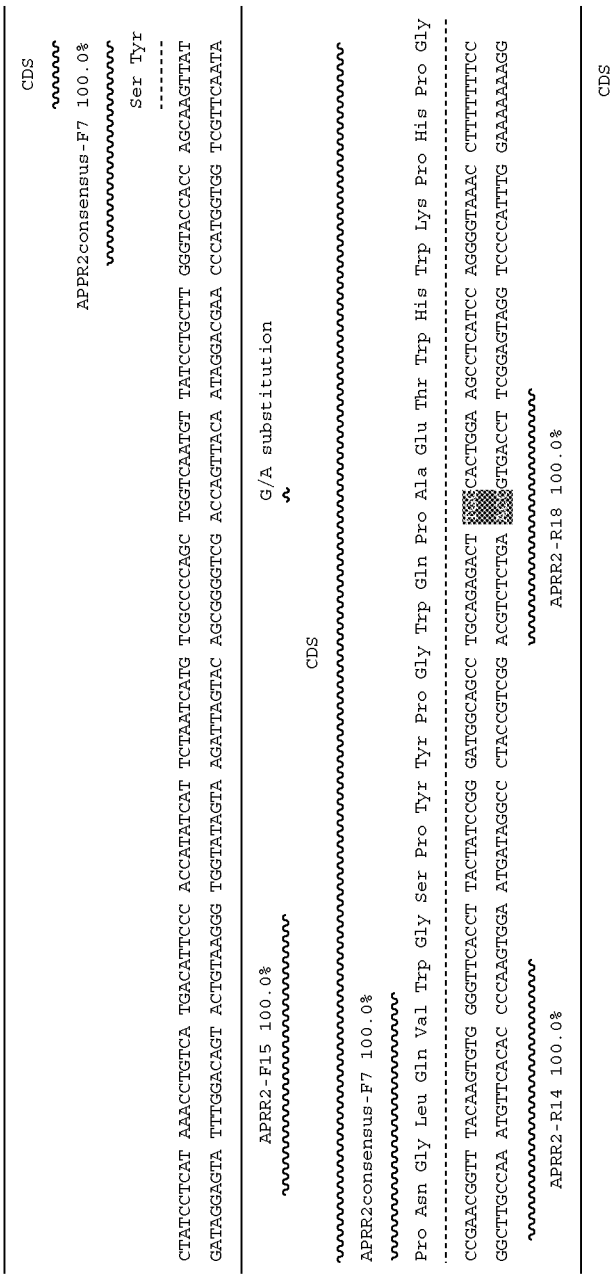

Wild type and truncation mutant pepper sequence are shown in SEQ ID NO: 14 and 16 respectively. Therefore it is concluded that the gene is truncated in the white parent. Further sequence analysis of the APRR2 gene across all individuals in the mature colour population reveals that all genotypes that have white immature fruit contain the stop codon. Distribution of the truncated genes in other types is less clear. No white immature fruit were found that do not have the truncation, so it is believed to be necessary for the white phenotype. The white colour phenotype caused by the G-A substitution is recessively inherited.

Example 12

Frequency of Presence of Red and White Alleles in Pepper

Figure 9:
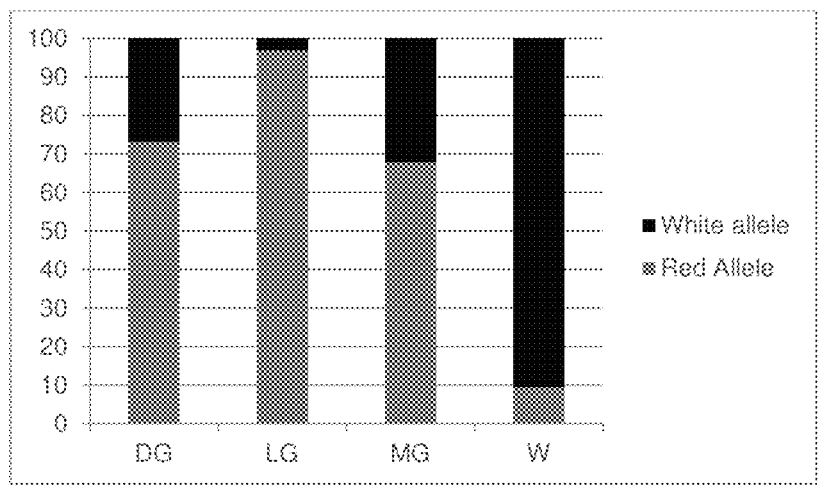
FIG. 9 Analysis of the presence of the A) APRR2 like gene and B) PSY1 gene from the white and red parent pepper lines across the mature colour mapping population. Frequency of presence of allele is shown on the y axis. Fruit colour is shown on the x axis. DG=dark green; LG=light green; MG=mature green; and W=white.
Figure 9:
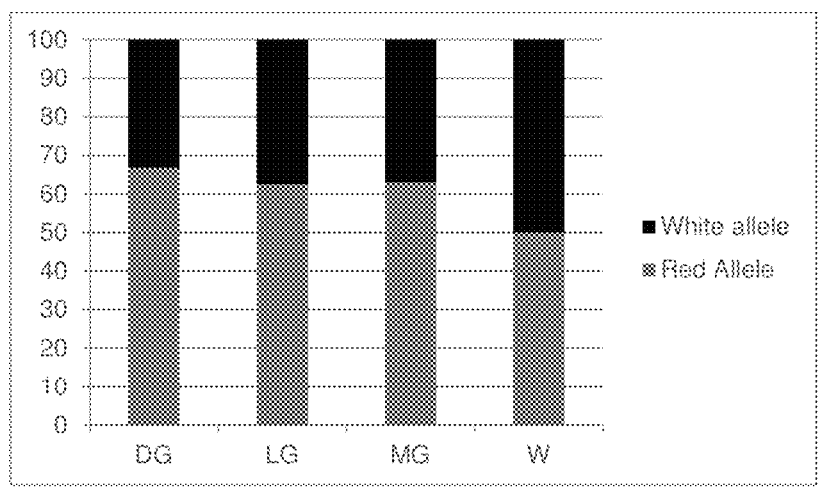

Analysis of the presence of the APRR2 like allele from the white or red parent across the mature colour mapping population reveals a correlation between the red or white allele and light green, or white immature fruit colour within the population (see FIG. 9). Presence of the red or white PSY1 allele is included for comparison. This gene doesn't correlate with immature colour types. It can be seen that the red allele is present at high frequency in light green immature fruit. The white allele is present at high frequency in white immature fruit.

Example 13 qRTPCR Analysis of Pepper Genes

The TaqMan-based real time assay was designed for use on ABI 7900HT Sequence Detection machines using Primer Express Software. A BLAST search of the amplicon was performed against the public Pepper DFCI and Syngenta proprietary databases. Only one hit was found with 100% match of entire amplicon sequence. The assay was validated using serial dilutions of RNA extracted from pooled leaf and fruit tissue. Reaction efficiency (1.01) and maximum fluorescence (3.5) both passed GM ADT validation parameters. Reactions were combined in a 10 ul volume using typical one-step RT-PCR reagents and thermocycler settings.

Example 14

Figure 10:
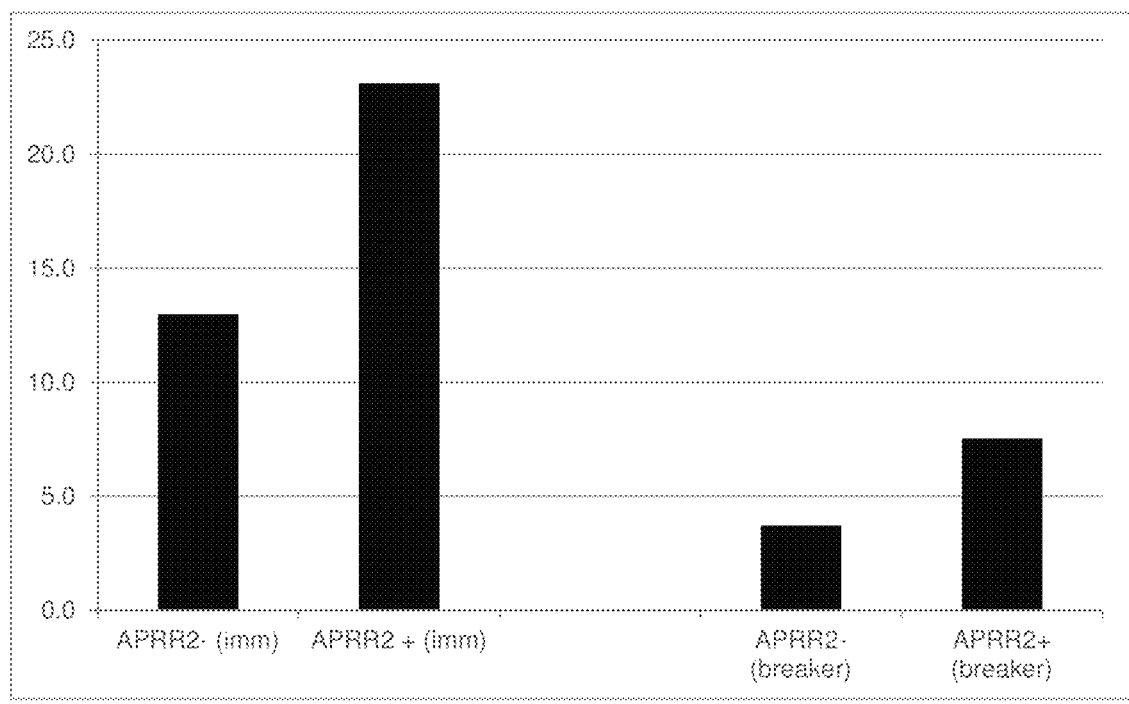
FIG. 10 qRTPCR analysis of APRR2 like gene expression in the mature colour pepper population at the immature (imm) and breaker stage. The bars represent the mean of a number of data points. Full gene sequence is represented by APRR2+. Truncated gene sequence in which the message encodes a stop codon is represented by APRR2−.

Expression Analysis Across Mature Colour Population of Pepper qRTPCR analysis of APRR2 like gene expression in the mature colour population revealed evidence for an increase in expression associated with the full gene sequence (APRR2+) in comparison to the truncated gene (APRR2−)—see FIG. 10. The figure shows the mean of a number of data points with a high coefficient of variance. This data supports the mRNA seq data where APRR2 expression is highest at the immature stage.

REFERENCES

Batu, A. and Thompson, A. K. 1998, Tr. J. Agr. & Forestry, 22, 365-372.
Doyle J J and Doyle J L (1990) Focus 12: 13-15.
Ebert et al., 1987 Proc. Natl. Acad. Sci. U.S.A. 84:5745-5749
Eckstein F (ed) (1991) Oligonucleotides and Analogues, A Practical Approach. Oxford Univ. Press, NY 1991.
Eriksson E M, Bovy A, Manning K, Harrison L, Andrews J, De Silva J, Tucker G A, Seymour G B, 2004 Plant Physiol.; 136(4):4184-97
Exama, A., Arul, J., Lencki, R. W., Lee, L. Z. and Toupin, C. 1993. J. Food Sci. 58: 1365-1370.
Forth D. and Pyke K. A. Journal of Experimental Botany, Vol. 57, No. 9, pp. 1971-1979, 2006
Frary A, Nesbitt T C, Grandillo S, Knaap E, Cong B, Liu J, Meller J, Elber R, Alpert K B, Tanksley S D 2000. Science; 289(5476):85-8.
Fray and Grierson, 1993 Plant Mol Biol.; 22(4):589-602.
Fridman E, Carrari F, Liu Y S, Fernie A R, Zamir D. 2004 Science; 305(5691):1786-9.
Gautier, L., et al. 2004 Bioinformatics 20307-315
Geeson, J. D., Browne, K. M., Maddison, K. I., Shepherd, J. and Guaraldi, F. 1985. J. Food Technol. 20:339-349.
Goeddel, Gene Expression Technology: Methods in Enzymology 185, Academic Press, San Diego, Calif. (1990).
Heidmann I, de Lange B, Lambalk J, Angenent G, Boutilier K (2011). Plant Cell Rep. June; 30 (6):1107-15
Huh J. H., B. C. Kang, S. H. Nahm, S. Kim, K. S. Ha, M. H. Lee and B. D. Kim TAG Theoretical and Applied Genetics 102, no 4,524-530,
Irizarry R A, Hobbs B, Collin F, Beazer-Barclay Y D, Antonellis K J, Scherf U, Speed T P. (2003) Biostatistics. April; 4(2):249-64.
Knapp S (2005) New nomenclature for Lycopersicon http://sgn.cornell.edu/about/*solanum*_nomenclature.pl
Lawton et al., 1987 Plant Mol Biol. 9:315-324
Manning K, Tör M, Poole M, Hong Y, Thompson A J, King G J, Giovannoni J J, Seymour G B. 2006. Nat Genet.; 38(8):948-52.
Nakagawa T, Suzuki T, Murata S at el, 2007 Biochemistry, 71(8)2095-2010
Nielsen et al. (1991. Science 254:1497-1500)
Odell et al., 1985 Nature 313:810-812
Pearson W R (1990) Methods in Enzymology 183: 63-98.
Pyke A and Leech R (1991) Plant Physiology, 96, 1193-1195.
Sambrook J, and Russell D W (2001). Molecular Cloning: A Laboratory Manual. New York, N.Y., USA., Cold Spring Harbor Laboratory Press.
Shimamoto K. et al., 1989. Nature 338:274-276
Smyth, G. K. (2005). Limma: Linear Models for microarray data. In: Bioinformatics and Computational Biology Solutions using R and Bioconductor, R. Gentleman, V. Carey, S. Dudoit,
R. Irizarry, W. Huber (eds.), Springer, New York, pages 397-420.
Smith T, Waterman M (1981) J. Mol. Biol: 147, 195-197.
Thompson, A. J., Tor, M., Barry, C. S., Vrebalov, J., Orfila, C., Jarvis, M. C., Giovannoni, J. J., Grierson, D. and Seymour, G. B. (1999). Plant Physiology 120:383-389.
Thompson A. J., Tor M, Barry C S, Vrebalov J, Orfila C, Jarvis M C, Giovannoni J J, Grierson D, Seymour G B. Science. 2002; 296(5566):343-6.
Tijssen P (1993) Hybridization With Nucleic Acid Probes. Part I. Theory and Nucleic Acid Preparation. In: Laboratory Techniques in Biochemistry and Molecular Biology. Elsevier.
Vrebalov J, Ruezinsky D, Padmanabhan V, White R, Medrano D, Drake R, Schuch W, Giovannoni J (2002) Science 296: 5566, 343-346

The invention claimed is:

1. A method of manipulating the speed of ripening or the pigment content of a pepper fruit produced by a pepper plant by genetically modifying a pepper APPR2 gene of SEQ ID NO: 2 or SEQ ID NO: 14 in said pepper plant, the method comprising:
   (a) generating by TILLING variant gene products of a pepper APPR2 gene of SEQ ID NO: 2 or SEQ ID NO: 14 in a plurality of pepper plants to produce a plurality of genetically modified pepper plants; and
   (b) selecting a pepper plant from the plurality of genetically modified pepper plants of a) with a decreased speed of ripening or decreased pigment content in pepper fruits produced by said plant as compared with a pepper plant having the pepper APPR2 gene of SEQ ID NO: 2 or SEQ ID NO: 14, thereby manipulating the speed of ripening or the pigment content of a pepper fruit produced by said genetically modified pepper plant.

2. The method of claim 1, wherein variant gene products are generated by TILLING of a pepper APPR2 gene of SEQ ID NO: 14.

* * * * *

SEQUENCE LISTING

<160> NUMBER OF SEQ ID NOS: 19

<210> SEQ ID NO 1
<211> LENGTH: 2090
<212> TYPE: DNA
<213> ORGANISM: Lycopersicon esculentum

<400> SEQUENCE: 1

```
gacccaccta actataatca acaaacgacc cttaaaagaa gaagaaaaaa caagaacaga      60
tgagctaagt cttcttcatt tcccaagaga tacaggattg aatagttaat gactgattaa     120
aaagtgaccg agttggaggg actaaaaagg atgcctittt agaaatgatt tgcattgaga     180
atgaattatt gggttggaaa gatttcccaa aggggcttaa agtcctactt cttgatgaag     240
atagcaactc tgctgctgag atgaaatcaa ggcttgagaa aatggactac atagtctact     300
cgttctgcaa cgagagcgaa gctttgactg caatctcaag caaatccgag ggctttcatg     360
ttgccattgt ggaggtaagt gcaggcaaca gtgatggggt tctacggtttt cttgaaagtg     420
ccaaagatct accaactata atgacatcaa atatacattc tcttagtacc atgatgaaat     480
gtattgcgct aggcgcagtt gagttccttc agaaaccatt gtcagatgat aaactcaaaa     540
atatatggca gcatgtagtt cacaaggcat tcaatactag aaaggatgtg tccaaatcac     600
ttgagccggt aaaagattct gtcctctcga tgctgcagtt acaactagaa atgggtgaag     660
cagatgacaa aagttcaaat ggaacagaac ctcccactgc agtagcggaa agcaatactg     720
aacagtcatc gggctgtgat aaataccctg ctccctcaac cccacaattg aaacaaggag     780
tgcgatccgt cgatgatggt gactgccatg atcatactat cttctcaact gaccaagaca     840
gtggggaaca tgatgctgac actaaatccg tcgaaactac ttataacaat tcacttgctg     900
agaataatgt ccaaacaagt cctactgtac agcaaggaga tattattttg aaagaggata     960
atgtttcatc tcctgatcta aagacggaga ctgatatcgc taccacttca cgaagtaacg    1020
actgccctga caatagcatt atgcattctg ctgaacctag taaagcatct ggtcctcata    1080
gttcaaatgg gactaaatcc aataggaaga agataaaggt agattggaca cctgaactac    1140
acaagaagtt tgttcaagca gtagagcaac tcggtataga tcaagccatt ccttctcgaa    1200
tactggacct gatgaaagta gagggcttaa cgagacataa cgtagctagc catctccaga    1260
aatacagaat gcatcgaaag caaattttgc caaaggaagt agaaagaaga tggcctaatc    1320
cgcaaccaat agattcagtc caaagaagtt actatcctca taaacctatc atgacattcc    1380
cacaatatca ttctaatcat gttgccccag gtggtcagtt ctatcctgct tgggtaacac    1440
cagcaagtta tccgaacggt ttacaagtgt ggggttcacc ttactatccg ggatggaaac    1500
ctgcagagac ttggcactgg acgcctcgtc cagagctgca tgctgataca tggggctccc    1560
ctatcatgtc accgtcgctt ggatcatatc caccatatcc tcagaatgct ggagtgtacc    1620
ggccacatgg aacacataac agatatagca tgctagagaa gtcgtttgat cttcacccgg    1680
cggatgaggt gattgataaa gtagtaaaag aggcaataac caaaccatgg ttaccacttc    1740
ctttgggcct aaaagctcct tcaacggaga gcgttcttga cgaactttct agacaaggga    1800
tctcaaccat tccttcacaa atcaacgact cccgttgtcg gagatgagat gacatgtcat    1860
tctaattttt tttgggtccc atagttggtg catgtcaaaa aaaataata atctccaatt    1920
acttgatgga catatgtacc atgacattac ccagtgaccc gagtgaccca gcgtatggc    1980
attgactcga cggtcaaaat cgagttgttg taaataatgg acccaaatat gggttttccc    2040
tttttgttg gcccaatttt agatgtttgg gccgatgagt gtgctccatt            2090
```

<210> SEQ ID NO 2
<211> LENGTH: 1515
<212> TYPE: DNA
<213> ORGANISM: Capsicum annuum

<400> SEQUENCE: 2

```
atgatttgca ttgaggatga attattgggt tggaaagatt tcccaaaggg gcttaaagtc    60
ctcctccttg atgaagatag cagctctgct gctgagatga aatcaaggct tgagaaaatg   120
gactatatag tctacacgtt ctgcaatgag agtgaagctt tgtctgcaat ctctagcaaa   180
tccgagggct tcatgttgc cattgtggag gtaagtgcag gcgataatga tggggtcctc    240
caatttcttg aaagtgccaa aaatctacca actataatga catcaaatat tcattctctc   300
agcacaatga tgaagtgtat tgcgcttggt gcagttgagt tccttcagaa accattatca   360
gatgacaaac tcaaaaatat atggcagcat gtagttcaca aggcattcaa tgctagaaag   420
gatgtgtccg gaccacttga gccggtaaaa gaatctcttc tttcgatgct acagctacaa   480
ccagaaaagg gtgaaccaga tgacaaaagt tcaaatggaa cagaacctct cattgcagtt   540
gcggacaaca ataccgaaca gtcatcgggc tgtgataaat accctgctcc ctcaaccccct  600
caattgaaac aaggagtgcg gtcagtggat gatagtgact gccatgatca tactatcttc   660
tcaactgacc aagacaatgg ggagcatgat ggtgacacta atccgtcga  aactacttat   720
aacaattcac ttgctgagaa tactgtccaa ataagtcctc ctgggcaaca agaagatata   780
attttgaaag aggagaatgg ttcatctcct catcaaacta tggaggctga tattactacc   840
tcttcacaaa gtaaagactg ccctgacaat agcattagtc attctgctga acctagtaaa   900
gcttctggtc cccatagctc aagtgggact aaatccaata gaaaaaggt gaaggtagat    960
tggacacctg aactacacaa aaagtttgtt caagcagtag agcaactcgg tatagatcaa  1020
gccattcctt ctcgaatact agacgtgatg aaagtggagg gcttaacgag acataacata  1080
gctagccatc tccagaaata cagaatgcat cggaggcaaa ttttgccaag ggaagtggaa  1140
aggagatggc cccatccgca acctagagat tcagtacaaa ggaattacta tcctcataaa  1200
cctgtcatga cattcccacc atatcattct aatcatgtcg ccccagctgg tcaatgttat  1260
cctgcttggg taccaccggc tagttatccg aatggtttac aagtgtgggg ttcaccttac  1320
tatccgggat ggcagcctgc agagacttgg cactggaagc ctcatccagg gctgcttgct  1380
gatacatggg gctcccctgt catgccacca tcgtttggat cgtatccacc atatccccag  1440
aatgctggaa tgtaccagtc tcacggaatg cataacagat atagcatgct agagaagtca  1500
ttcgatgttc acccg                                                   1515
```

<210> SEQ ID NO 3
<211> LENGTH: 326
<212> TYPE: DNA
<213> ORGANISM: Lycopersicon esculentum

<400> SEQUENCE: 3

```
cacaatatca ttctaatcat gttgccccag gtggtcagtt ctatcctgct tgggtaacac    60
cagcaagtta tccgaacggt ttacaagtgt ggggttcacc ttactatccg ggatggaaac   120
ctgcagagac ttggcactgg acgcctcgtc cagagctgca tgctgataca tggggctccc   180
ctatcatgtc accgtcgctt ggatcatatc caccatatcc tcagaatgct ggagtgtacc   240
ggccacatgg aacacataac agatatagca tgctagagaa gtcgtttgat cttcacccgg   300
```

```
cggatgaggt gattgataaa gtagta                                          326
```

<210> SEQ ID NO 4
<211> LENGTH: 29
<212> TYPE: DNA
<213> ORGANISM: Artificial Sequence
<220> FEATURE:
<223> OTHER INFORMATION: Sequence attB1

<400> SEQUENCE: 4

```
ggggacaagt ttgtacaaaa aagcaggct                                       29
```

<210> SEQ ID NO 5
<211> LENGTH: 29
<212> TYPE: DNA
<213> ORGANISM: Artificial Sequence
<220> FEATURE:
<223> OTHER INFORMATION: Sequence attB2

<400> SEQUENCE: 5

```
ggggaccact ttgtacaaga aagctgggt                                       29
```

<210> SEQ ID NO 6
<211> LENGTH: 22
<212> TYPE: DNA
<213> ORGANISM: Artificial Sequence
<220> FEATURE:
<223> OTHER INFORMATION: npt II forward

<400> SEQUENCE: 6

```
caccatgata ttcggcaagc ag                                              22
```

<210> SEQ ID NO 7
<211> LENGTH: 22
<212> TYPE: DNA
<213> ORGANISM: Artificial Sequence
<220> FEATURE:
<223> OTHER INFORMATION: npt II reverse primer

<400> SEQUENCE: 7

```
tgtgctcgac gttgtcactg aa                                              22
```

<210> SEQ ID NO 8
<211> LENGTH: 24
<212> TYPE: DNA
<213> ORGANISM: Artificial Sequence
<220> FEATURE:
<223> OTHER INFORMATION: LeELF-F

<400> SEQUENCE: 8

```
acctttgctg aataccctcc attg                                            24
```

<210> SEQ ID NO 9
<211> LENGTH: 24
<212> TYPE: DNA
<213> ORGANISM: Artificial Sequence
<220> FEATURE:
<223> OTHER INFORMATION: LeELF-R

<400> SEQUENCE: 9

```
cacacttcac ttccccttct tctg                                            24
```

<210> SEQ ID NO 10
<211> LENGTH: 27
<212> TYPE: DNA
<213> ORGANISM: Artificial Sequence
<220> FEATURE:
<223> OTHER INFORMATION: LeELF probe (FAM)

<400> SEQUENCE: 10
tcgttttgct gtgagggaca tgaggca                                           27

<210> SEQ ID NO 11
<211> LENGTH: 23
<212> TYPE: DNA
<213> ORGANISM: Artificial Sequence
<220> FEATURE:
<223> OTHER INFORMATION: 5930-Q-F

<400> SEQUENCE: 11
ttgccccagg tggtcagttc tat                                               23

<210> SEQ ID NO 12
<211> LENGTH: 23
<212> TYPE: DNA
<213> ORGANISM: Artificial Sequence
<220> FEATURE:
<223> OTHER INFORMATION: 5930-Q-R

<400> SEQUENCE: 12
cagtgccaag tctctgcagg ttt                                               23

<210> SEQ ID NO 13
<211> LENGTH: 27
<212> TYPE: DNA
<213> ORGANISM: Artificial Sequence
<220> FEATURE:
<223> OTHER INFORMATION: 5930-Q-probe

<400> SEQUENCE: 13
atccgaacgg tttacaagtg tggggtt                                           27

<210> SEQ ID NO 14
<211> LENGTH: 5787
<212> TYPE: DNA
<213> ORGANISM: Capsicum annuum

<400> SEQUENCE: 14
tttcccctaa aaagatcta ttacatgggg ttttttctgt tttatgttgg ttcttattta         60
aagctgaaaa tagtctttgt ctctttcctt ttttgttaga tgatgttgaa gattcaagct       120 tgaaaagtg tgtcagaagg agtggggggg gggggggttg attttttttg tttattttga       180
gacatgtact attattatga gtgatattta ctgtaaggtt taagagggat tttgctaaag       240
gttgaatttt taatgtaaat ctgaggggaa ttccttttg gatgtgcaga ttcaattggt        300
aatgactgat taagtgactg ttttggagg cactaatttg gctgacctaa aaaggatgcc        360 ttttagaaa tgatttgcat tgaggatgaa ttattgggtt ggaaagattt cccaaagggg       420
cttaaagtcc tcctccttga tgaagatagc agctctgctg ctgagatgaa atcaaggctt       480
gagaaaatgg actatatagg taagtagttg taacccagtc taaaaatact tactcgcacc       540
cggtgtttat gtttttttt tttctttttgg ttttgctcat tccttttggt gttgcctgta       600
aagttgctgc aatatgacta ggaggtcaga aacagcctct tgctgaaatg caaggtaagg       660
ctgcgtacaa taaactcatg tagttcgaca cttttcctatg catatcggga gttttggtgc     720
acggggctgc cctcatccct tttggtacaa aattttttgg tttagtcact ttctgttttg      780
caagttagtt gtgcatttct tggtctgttt cttgttgat ttctccttat atagaagttc       840

-continued

```
ctttacattt attacttagg gaaaatagag tattctgatt catcttttct attttaagac    900
aaaacattta agtggttcag gattcatact tctacctttt cctggaatgc tgcagaggtc    960
ctctaacaag atagaatttg aacttccctt tatggttctt gcaagtttat actccctcgg   1020
tttcaatttg tttgtctggc cttgactcag gggcggacct acatggtcca tgccgggtgc   1080
ttgagcaacc aatgacccct caagtgatgt ggattcgatt cctggtagca acactttttt   1140
ttcgtaaagg aattgagcac ccacaacctt caaatcctgg atccgcgctg ctttgacttg   1200
acacgaagtt taagaaagta aatgagtctg aatcttgtgg tcttaaacta agataagct    1260
aaaacaaata aattgaaact gagggaatat ctatttatga tgtttcaaaa tttgggttaa   1320
ttagttgctt cacattagca gatattgaat gattcactgt tgaatgctct gaattaccgt   1380
agttatcaaa tttgttttc attctttctt taacctttga agtaatgtga ctagcggaat    1440
atagtttctt tgaagcaaca acttatttta tgattaggat gacattttgc tcagtcctta   1500
gcttgttttt tttccacaaa attgttcttg aatttgtttc atttcgcgga tcttcctgaa   1560
aggtcattat tatattcata tgctataaac ccaccatgta attgcagtct acacgttctg   1620
caatgagagt gaagctttgt ctgcaatctc tagcaaatcc gagggctttc atgttgccat   1680
tgtgaggta gtagttacat ttttacttga aactttccat attcaccttt atggtaagac   1740
tattgatcaa caaatatat tgatcaacaa aatatgaaga caggccagaa tgttattcta    1800
actgttgatg aatttgtcta tcaattgaca caggtaagtg caggcgataa tgatggggtc   1860
ctccaatttc ttgaaagtgc caaaaatcta ccaactataa gtgagtgcta tatatacgaa   1920
aaaataagtg gcgtattgca agttgactta gtttcagcag atatgatagt attggcagag   1980
ttagaagtgc tagaatctta agtcttccaa ctatcacgta gaccactgaa cttggaatat   2040
tttgcttgtc ttcaaatgtt taaacgctat aacatatcta agggagcttt gtttacttcg   2100
tgcagtgaca tcaaatattc attctctcag cacaatgatg aagtgtattg cggtgaactc   2160
ttggggctca aattttcatt tgatgctaac tgtttctggt aattatgtgt gaaagatgtt   2220
caatgcttcg atattttgca gcttggtgca gttgagttcc ttcagaaacc attatcagat   2280
gacaaactca aaaatatatg gcagcatgta gttcacaagg tttgtaatcc aaacttcaca   2340
caatcagctt agttctttca aatcagtatg cttattatat gaaaaggaaa tcctgatctt   2400
attggttgca acaggcattc aatgctagaa aggatgtgtc cggaccactt gagccggtaa   2460
aagaatctct tctttcgatg ctacagctac aaccagaaaa gggtgaacca gatgacaaaa   2520
gttcaaatgg aacagaacct ctcattgcag ttgcggacaa caataccgaa cagtcatcgg   2580
gctgtgataa ataccctgct ccctcaaccc ctcaattgaa acaaggagtg cggtcagtgg   2640
atgatagtga ctgccatgat catactatct tctcaactga ccaagacaat ggggagcatg   2700
atggtgacac taaatccgtc gaaactactt ataacaattc acttgctgag aatactgtcc   2760
aaataagtcc tcctgggcaa caagaagata taatttgaa agaggagaat ggttcatctc    2820
ctcatcaaac tatggaggct gatattgcta ccttttcaca aattaatgac tgcgctgaca   2880
atagtgatgg ttcatctcct catcaaaaga cggaggctga tattgctact acctcttcac   2940
aaagtaaaga ctgccctgac aatagcatta gtcattctgc tgaacctagt aaagcttctg   3000
gtccccatag ctcaagtggg actaaatcca ataagaaaaa ggtgaaggta agatggaaga   3060
aatgatactt tggttctcat agtacaataa tgaagtaact acgcactcaa cggtccgtaa   3120
tattagtgtc caagaatgcc attatgtttt gtctactggt tccgaaggta taagaatgtt   3180
gcataacttt cgcatgcatt cttaaaacat gtttcatgat tgcttctctt gctcatcagt   3240
```

```
catacggtct tttgttattt atctcttctt tctataaaag gggatgagat gaagatatta    3300
catgtggcat tgcgtgtatc tttctcctct tgcattaacg aatttagcct tatgaactgt    3360
taagttctta gagaacttca tggctatcat agaacatcct tttcaagttc catttcgtct    3420
atgatttatc aattacagtg gatctttcaa gattctgctt aaagcacctt taagatgaat    3480
gcgaggctca ttttgttatc tcgaagtttg aacttctcaa acggtgtatg aatctataat    3540
atggtaatca gtataggaat ttagctagag ttgtgttggg gatttcagcc ttaaatgtag    3600
ttgactgagc agcggtgaaa caattctgca ttcttcgaag tttgaattgc gtgtttcagg    3660
gggataagtt tggtatttcc tttggattca ggtagattgg acacctgaac tacacaaaaa    3720
gtttgttcaa gcagtagagc aactcggtat agatcaagcc attccttctc gaatactaga    3780
cgtgatgaaa gtggagggct taacgagaca taacatagct agccatctcc aggtttgtga    3840
gttctgctct ttcatatctt aatgaatatg tttgctatgt ttggcagcgt cggaagcaat    3900
ttggctgaaa gatgtcttaa tataaatgtt ctaacattgg ggaaaacgcg atagtactaa    3960
atcttgacca ttttcagcct gttggcacct caagttagat aaatattcat ttgatatttc    4020
catatccttg gaggggatgt agtatagcag ttgtgctaca aaaaagttgg atgttgataa    4080 tattttccg tttaacaata gtatcacctt tcaatttcca agcagaaata cagaatgcat    4140
cggaggcaaa ttttgccaag ggaagtggaa aggagatggc cccatccgca acctagagat    4200
tcagtacaaa ggaattacta tcctcataaa cctgtcatga cattcccacc atatcattct    4260
aatcatgtcg ccccagctgg tcaatgttat cctgcttggg taccaccggc tagttatccg    4320
aatggtttac aagtgtgggg ttcaccttac tatccgggat ggcagcctgc agagacttgg    4380
cactggaagc ctcatccagg ggtaaacctt ttttttccctt agaccacatt gcatgcctat    4440
gtcaacatat ttcacaggat atttttaggtc taggaaatac cacacctaaa aacttatgtt    4500
ttgtaataat gcagctgctt gctgatacat ggggctcccc tgtcatgcca ccatcgtttg    4560
gatcgtatcc accatatccc caggtgagtt cattggcaat atcacccc cgttagatat    4620 ttttatgttc aatatgacaa cgttcttgag atatttcatg tgaatgcact cttgggttga    4680
gttcttaatg gcacatcggt tggatgatgc agaatgctgg aatgtaccag tctcacggaa    4740
tgcataacag atatagcatg ctagagaagt cattcgatgt tcacccggta agattgtaga    4800
tcctatttca gaccgacaaa cttctttata cataaatgca ctaggagatt attcatattc    4860
cagtttcgtt ttccctttg gagctacaaa ggaaaaacac aacgtaaatg ttttatggct    4920
tatgttgtat taagtgaagg aaaatgtttt tcaattttc gatgttccac tggtcaaaag    4980
ttttgaaaaa tattttctct agaaaaataa gttgcttgaa aaatgagaaa atgacatttt    5040
ctagtggaag taaggaaaac aagttccacc tgtggcattc cacattgatt gtgttctcat    5100
tcctcccaat actccaacac acttcatctt cacccctacc ctcgtagctc catgcccacc    5160
gtccataata ttctctagat tatatacaaa tactttaagg acaatgtttt tttgtttacg    5220
tgccgaacac tagaaaataa gtaagaaccg aacataagaa agtacgtttc taagtaagaa    5280
actcactcat tttcctagaa aatattttcc acgaaaacat tgttcgtgga aacattttc    5340 cttcatacca aacacaccct tagccctaga attcattcga taatcgtgcc aaaactacat    5400
atgtgtaatg aagggggaggc actgggttaa acttgaccaa tcatctccaa aatggatcta    5460
aattacatac aatacaacta cactgctaac gtactcagtg caatctcatg agtggctaaa    5520
ttacatacaa tcaccgggta aaaagagaat atattatttg actagtatgt ataattagtt    5580
```

```
gtcacattgg tttaagaagg ggttatagtg tcttggacaa cccttaccat gctagctttt    5640
gaggtttgat taggcctaag gtccatttta tcataactag attatcgacc cccacccccc    5700
cggtacacta tagctagtat tggtctccta gtaacttgat agtataaaat tttttattgg    5760
ttaagttttg gttggtggtg tgtgcag                                        5787
```

<210> SEQ ID NO 15
<211> LENGTH: 1515
<212> TYPE: DNA
<213> ORGANISM: Capsicum annuum

<400> SEQUENCE: 15

```
atgatttgca ttgaggatga attattgggt tggaaagatt tcccaaaggg gcttaaagtc      60
ctcctccttg atgaagatag cagctctgct gctgagatga aatcaaggct tgagaaaatg     120
gactatatag tctacacgtt ctgcaatgag agtgaagctt tgtctgcaat ctctagcaaa     180
tccgagggct ttcatgttgc cattgtggag gtaagtgcag gcgataatga tggggtcctc     240
caatttcttg aaagtgccaa aaatctacca actataatga catcaaatat tcattctctc     300
agcacaatga tgaagtgtat tgcgcttggt gcagttgagt tccttcagaa accattatca     360
gatgacaaac tcaaaaatat atggcagcat gtagttcaca aggcattcaa tgctagaaag     420
gatgtgtccg gaccacttga gccggtaaaa gaatctcttc tttcgatgct acagctacaa     480
ccagaaaagg gtgaaccaga tgacaaaagt tcaaatggaa cagaacctct cattgcagtt     540
gcggacaaca ataccgaaca gtcatcgggc tgtgataaat accctgctcc ctcaaccccct    600 caattgaaac aaggagtgcg gtcagtggat gatagtgact gccatgatca tactatcttc     660
tcaactgacc aagacaatgg ggagcatgat ggtgacacta atccgtcga aactacttat      720 aacaattcac ttgctgagaa tactgtccaa ataagtcctc ctgggcaaca agaagatata     780
attttgaaag aggagaatgg ttcatctcct catcaaacta tggaggctga tattactacc     840
tcttcacaaa gtaaagactg ccctgacaat agcattagtc attctgctga acctagtaaa     900
gcttctggtc cccatagctc aagtgggact aaatccaata agaaaaaggt gaaggtagat     960
tggacacctg aactcacaca aaagtttgtt caagcagtag agcaactcgg tatagatcaa    1020
gccattcctt ctcgaatact agacgtgatg aaagtggagg gcttaacgag acataacata    1080
gctagccatc tccagaaata cagaatgcat cggaggcaaa ttttgccaag ggaagtggaa    1140
aggagatggc cccatccgca acctagagat tcagtacaaa ggaattacta tcctcataaa    1200
cctgtcatga cattcccacc atatcattct aatcatgtcg ccccagctgg tcaatgttat    1260
cctgcttggg taccaccggc tagttatccg aatggtttac aagtgtgggg ttcaccttac    1320
tatccgggat ggcagcctgc agagacttga cactggaagc ctcatccagg gctgcttgct    1380
gatacatggg gctcccctgt catgccacca tcgtttggat cgtatccacc atatccccag    1440
aatgctggaa tgtaccagtc tcacggaatg cataacagat atagcatgct agagaagtca    1500
ttcgatgttc acccg                                                    1515
```

<210> SEQ ID NO 16
<211> LENGTH: 5773
<212> TYPE: DNA
<213> ORGANISM: Capsicum annuum

<400> SEQUENCE: 16

```
tttcccctaa aaaagatcta ttacatgggg ttttttctgt tttatgttgg ttcttattta      60
aagctgaaaa tagtctttgt ctctttcctt ttttgttaga tgatgttgaa gattcaagct     120
```

```
tgaaaaagtg tgtcagaagg agtgggggggg ggggggttga ttttttttgt ttattttgag      180
acatgtacta ttattatgag tgatatttac tgtaaggttt aagagggatt ttgctaaagg      240
ttgaattttt aatgtaaatc tgagggaat tccttttgg atgtgcagat tcaattggta       300
atgactgatt aagtgactgt ttttggaggc actaatttgg ctgacctaaa aaggatgcct      360
ttttagaaat gatttgcatt gaggatgaat tattgggttg gaaagatttc ccaaaggggc      420
ttaaagtcct cctccttgat gaagatagca gctctgctgc tgagatgaaa tcaaggcttg      480
agaaaatgga ctatataggt aagtagttgt aacccagtct aaaaatactt actcgcaccc      540
ggtgtttatg tttttttttt ttcttttggt tttgctcatt cctttggtg ttgcctgtaa       600 agttgctgca atatgactag gaggtcagaa acagcctctt gctgaaatgc aaggtaaggc      660
tgcgtacaat aaactcatgt agttcgacac tttcctatgc atatcgggag ttttggtgca      720
cggggctgcc ctcatccctt ttggtacaaa attttttggt ttagtcactt tctgttttgc      780
aagttagttg tgcatttctt ggtctgtttc tttgttgatt tctccttata tagaagttcc      840
tttacattta ttacttaggg aaaatagagt attctgattc atcttttcta ttttaagaca      900
aaacatttaa gtggttcagg attcatactt ctaccttttc ctggaatgct gcagaggtcc      960
tctaacaaga tagaatttga acttcccttt atggttcttg caagtttata ctccctcggt     1020
ttcaatttgt ttgtctggcc ttgactcagg ggcggaccta catggtccat gccgggtgct     1080
tgagcaacca atgacccctc aagtgatgtg gattcgattc ctggtagcaa cactttttt     1140 tcgtaaagga attgagcacc cacaaccttc aaatcctgga tccgcgctgc tttgacttga     1200
cacgaagttt aagaaagtaa atgagtctga atcttgtggt cttaaactaa agataagcta     1260
aaacaaataa attgaaactg agggaatatc tatttatgat gtttcaaaat ttgggttaat     1320
tagttgcttc acattagcag atattgaatg attcactgtt gaatgctctg aattaccgta     1380
gttatcaaat ttgttttca ttctttcttt aacctttgaa gtaatgtgac tagcggaata     1440
tagtttcttt gaagcaacaa cttattttat gattaggatg acattttgct cagtccttag     1500
cttgtttttt ttccacaaaa ttgttcttga atttgtttca tttcgcggat cttcctgaaa     1560
ggtcattatt atattcatat gctataaacc caccatgtaa ttgcagtcta cacgttctgc     1620
aatgagagtg aagctttgtc tgcaatctct agcaaatccg agggctttca tgttgccatt     1680
gtggaggtag tagttacatt tttacttgaa actttccata ttcaccttta tggtaagact     1740
attgatcaac aaaatatatt gatcaacaaa atatgaagac aggccagaat gttattctaa     1800
ctgttgatga atttgtctat caattgacac aggtaagtgc aggcgataat gatgggtcc      1860 tccaatttct tgaaagtgcc aaaaatctac caactataag tgagtgctat atatacgaaa     1920
aaataagtgg cgtattgcaa gttgacttag tttcagcaga tatgatagta ttggcagagt     1980
tagaagtgct agaatcttaa gtcttccaac tatcacgtag accactgaac ttggaatatt     2040
ttgcttgtct tcaaatgttt aaacgctata acatatctaa gggagctttg tttacttcgt     2100
gcagtgacat caaatattca ttctctcagc acaatgatga agtgtattgc ggtgaactct     2160 tgggctcaa atttcatttt gatgctaact gttctggta attatgtgtg aaagatgttc       2220
aatgctttga tattttgcag cttggtgcag ttgagttcct tcagaaacca ttatcagatg     2280
acaaactcaa aaatatatgg cagcatgtag ttcacaaggt ttgtaatcca aacttcacac     2340
aatcagctta gttctttcaa atcagtatgc ttattatatg aaaaggaaat cctgatctta     2400
ttggttgcaa caggcattca atgctagaaa ggatgtgtcc ggaccacttg agccggtaaa     2460
```

```
agaatctctt ctttcgatgc tacagctaca accagaaaag ggtgaaccag atgacaaaag    2520
ttcaaatgga acagaacctc tcattgcagt tgcggacaac aataccgaac agtcatcggg    2580
ctgtgataaa taccctgctc cctcaaccc tcaattgaaa caaggagtgc ggtcagtgga     2640
tgatagtgac tgccatgatc atactatctt ctcaactgac caagacaatg gggagcatga   2700
tggtgacact aaatccgtcg aaactactta taacaattca cttgctgaga atactgtcca   2760
aataagtcct cctgggcaac aagaagatat aattttgaaa gaggagaatg gttcatctcc   2820
tcatcaaact atggaggctg atattgctac cttttcacaa attaatgact gcgctgacaa   2880
tagtgatggt tcatctcctc atcaaaagac ggaggctgat attgctacta cctcttcaca   2940
aagtaaagac tgccctgaca atagcattag tcattctgct gaacctagta aagcttctgg   3000
tccccatagc tcaagtggga ctaaatccaa taagaaaaag gtgaaggtaa gatggaagaa   3060
atgatacttt ggttctcata gaacaataat gaagtaacta cgcactcaac gttctgtaat   3120
attattgtcc aagaatgcca ttatgttttg tctactggtt ccgaaggtat aagaatgttg   3180 cataacttc gcatgcattc ttaaaacatg tttcatgatt gcttctcttg ctcatcagtc    3240
atacggtctt ttgttattta tctcttcttt ctataaaagg ggatgagatg aagatattac   3300
atgtggcatt gcgtgtatct ttctcctctt gcattaacga atttagcctt atgaactgtt   3360
aagttcttag agaacttcat ggctatcata gaacatcctt ttcaagttcc atttcgtcta   3420
tgatttatca attacagtgg atcttcaag attctgctta aagcaccttt aagatgaatg     3480
cgaggctcat tttgttatct cgaagtttga acttctcaaa cggtgtatga atctataata   3540
tggtaatcag tataggaatt tagctagagt tgtgttgggg atttcagcct taaatgtagt   3600
tgactgagca gcggtgaaac aattctgcat tcttcgaagt ttgaattgcg tgtttcaggg   3660
ggataagttt ggtatttcct ttggattcag gtagattgga cacctgaact acacaaaaag   3720
tttgttcaag cagtagagca actcggtata gatcaagcca ttccttctcg aatactagac   3780
gtgatgaaag tggagggctt aacgagacat aacatagcta gccatctcca ggtttgtgag   3840
ttctgctctt tcatatctta atgaatatgt ttgctatgtt tggcagcgtc ggaagcaatt   3900
tggctgaaag atgtcttaat ataaatgttc taacattggg gaaaacgcga tagtactaaa   3960
tcttgaccat tttcagcctg ttggcacctc aagttagata aatattcatt tgatatttcc   4020
atatccttgg aggggatgta gtatagcagt tgtgctacaa aaaagttgga tgttgataat   4080 attttttccgt ttaacaatag tatcaccttt caatttccaa gcagaaatac agaatgcatc   4140
ggaggcaaat tttgccaagg gaagtggaaa ggagatggcc ccatccgcaa cctagagatt   4200
cagtacaaag gaattactat cctcataaac ctgtcatgac attcccacca tatcattcta   4260
atcatgtcgc cccagctggt caatgttatc ctgcttgggt accaccggct agttatccga   4320
atggtttaca agtgtggggt tcaccttact atccgggatg gcagcctgca gagacttgac   4380
actggaagcc tcatccaggg gtaaaccttt ttttcccctta gaccacattg catgcctatg   4440
tcaacatatt tcacaggata ttttaggtct aggaaatacc acacctaaaa acttatgttt   4500
tgtaataatg cagctgcttg ctgatacatg gggctcccct gtcatgccac catcgtttgg   4560
atcgtatcca ccatatcccc aggtgagttc attggcaata tcaccccc gttagatatt     4620 tttatgttca gtatgacaac gttcttgaga tatttcatgt gaatgcactc ttgggttgag   4680
ttcttaatgg cacatcggtt ggatgatgca gaatgctgga atgtaccagt ctcacggaat   4740
gcataacaga tatagcatgc tagagaagtc attcgatgtt cacccggtaa gattgtgat    4800 cctatttcag accgacaaac ttctttatac ataaatgcac taggagatta ttcatattcc    4860
```

```
agtttcgttt tcccttttgg agctacaaag gaaaaacaca acgtaaatgt tttatggctt    4920
atgttgtatt aagtgaagga aaatgttttt caattttcg atgttccact ggtcaaaagt     4980
tttgaaaaat attttctcta gaaaataag ttgcttgaaa aatgagaaaa atgacatttc     5040
tagtggaagt aaggaaaaca agttccacct gtggcattcc acattgattg tgttctcatt    5100
cctcccaata ctccaacaca cttcatcttc acccctaccc tcgtagctcc atgcccaccg    5160
tccataatat tctctagatt atatacaaat actttaagga caatgttttt ttgtttacgt    5220
gccgaacact agaaaataag taagaaccga acataagaaa gtacgtttct aagtaagaaa    5280
ctcactcatt ttcctagaaa atattttcca cgaaaacatt gttcgtggaa acatttttcc    5340
ttcataccaa acacaccctt agccctagaa ttcattcgat aatcgtgcca aaactacata    5400
tgtgtaatga aggggaggca ctgggttaaa cttgaccaat catctccaaa atggatctaa    5460
attacataca atacaacaac actactaacg tactcagtgc aatctcatga gtggctaaat    5520
tacatacaat caccgggtaa aaagagaata tattatttga ctagtatgta taattagttg    5580
tcacattggt ttaagaaggg gttatagtgt cttggacaac ccttaccatg ctagcttttg    5640
aggtttgatt aggcctaagg tccatttat cataactaga ttatcgaccc ccacccccc     5700 ggtacactat agctagtatt ggtctcctag taacttgata gtataaaatt ttttattggt    5760
taagttttgg ttg                                                       5773

<210> SEQ ID NO 17
<211> LENGTH: 23
<212> TYPE: DNA
<213> ORGANISM: Artificial Sequence
<220> FEATURE:
<223> OTHER INFORMATION: forward primer to make probe from the 3' end
      of the EST sequence (example 11)

<400> SEQUENCE: 17
ggtttacaag tgtggggttc acc                                            23

<210> SEQ ID NO 18
<211> LENGTH: 26
<212> TYPE: DNA
<213> ORGANISM: Artificial Sequence
<220> FEATURE:
<223> OTHER INFORMATION: reverse primer to make probe from the 3' end
      of the EST sequence (example 11)

<400> SEQUENCE: 18
catcgaatga cttctctagc atgcta                                         26

<210> SEQ ID NO 19
<211> LENGTH: 30
<212> TYPE: PRT
<213> ORGANISM: Lycopersicon esculentum

<400> SEQUENCE: 19

Ser Tyr Pro Asn Gly Leu Gln Val Trp Gly Ser Pro Tyr Tyr Pro Gly
1               5                   10                  15

Trp Gln Pro Ala Glu Thr Trp His Trp Lys Pro His Pro Gly
            20                  25                  30
```